United States Patent
Gao et al.

(10) Patent No.: US 11,740,240 B2
(45) Date of Patent: Aug. 29, 2023

(54) IMMUNOASSAY FOR SARS-COV-2 NEUTRALIZING ANTIBODIES AND MATERIALS THEREFOR

(71) Applicant: BIO-RAD LABORATORIES, INC., Hercules, CA (US)

(72) Inventors: Qian Gao, Concord, CA (US); Ravi Kaul, Davis, CA (US); Shuxia Zhou, Benicia, CA (US); Roger P. Walker, Benicia, CA (US)

(73) Assignee: BIO-RAD LABORATORIES, INC., Hercules, CA (US)

( * ) Notice: Subject to any disclaimer, the term of this patent is extended or adjusted under 35 U.S.C. 154(b) by 0 days.

(21) Appl. No.: 17/379,193

(22) Filed: Jul. 19, 2021

(65) Prior Publication Data

US 2022/0018838 A1    Jan. 20, 2022

Related U.S. Application Data

(60) Provisional application No. 63/114,685, filed on Nov. 17, 2020, provisional application No. 63/088,195,
(Continued)

(51) Int. Cl.
*G01N 33/569* (2006.01)
*G01N 21/64* (2006.01)

(52) U.S. Cl.
CPC ... *G01N 33/56983* (2013.01); *G01N 21/6428* (2013.01); *G01N 2021/6439* (2013.01); *G01N 2333/165* (2013.01)

(58) Field of Classification Search
CPC ......... G01N 33/56983; G01N 21/6428; G01N 2021/6439; G01N 2333/165;
(Continued)

(56) References Cited

U.S. PATENT DOCUMENTS 5,356,713 A * 10/1994 Charmot ................. C08K 9/10
428/407
6,649,414 B1 * 11/2003 Chandler ............. G01N 33/587
436/805
(Continued)

FOREIGN PATENT DOCUMENTS

CN         111187354         5/2020
CN         111273006         6/2020
(Continued)

OTHER PUBLICATIONS

International Search Report and Written Opinion in International Application No. PCT/US2021/42170, dated Feb. 7, 2022, pp. 1-15.
(Continued)

*Primary Examiner* — David P Porta
*Assistant Examiner* — Djura Malevic
(74) *Attorney, Agent, or Firm* — SALIWANCHIK, LLOYD & EISENSCHENK

(57) ABSTRACT

The present invention relates to the development of novel immunoassays for the detection of neutralizing antibodies and/or high avidity neutralizing antibodies to SARS-CoV-2 spike protein variants or fragments thereof and, optionally, one or more cytokine in patient samples. Novel multiplex and singleplex immunoassays for the detection of neutralizing antibodies and/or high avidity neutralizing antibodies to SARS-CoV-2 spike protein variants or fragments thereof and, optionally, one or more cytokine in patient samples are also provided.

21 Claims, 8 Drawing Sheets

Specification includes a Sequence Listing.

Related U.S. Application Data filed on Oct. 6, 2020, provisional application No. 63/053,888, filed on Jul. 20, 2020.

(58) Field of Classification Search
CPC ......... G01N 2333/948; G01N 2469/20; G01N 21/00; G01N 21/62; G01N 21/63; G01N 21/64; G01N 21/6439; G01N 21/6476; G01N 21/6486; G01N 33/58; G01N 33/581; G01N 33/582; G01N 33/585; G01N 33/53

See application file for complete search history.

(56) References Cited

U.S. PATENT DOCUMENTS

| | | | |
|---|---|---|---|
| 6,939,720 B2* | 9/2005 | Chandler | G01N 15/1012 435/6.12 |
| 7,722,886 B2* | 5/2010 | Siber | C07K 16/241 424/221.1 |
| 8,227,602 B2* | 7/2012 | Gautier | C07D 403/14 544/317 |
| 8,877,511 B2* | 11/2014 | Bedre | H01F 1/00 436/172 |
| 9,109,219 B2* | 8/2015 | Despres | C12N 5/0601 |
| 9,465,036 B2* | 10/2016 | Winnik | G01N 33/6848 |
| 9,638,692 B2* | 5/2017 | Manuguerra | G01N 33/56983 |
| 9,823,246 B2* | 11/2017 | Dai | G01N 33/553 |
| 10,017,769 B2* | 7/2018 | Despres | C12N 15/85 |
| 10,067,135 B2* | 9/2018 | Kaul | G01N 33/5761 |
| 10,088,478 B2* | 10/2018 | Dai | G01N 21/648 |
| 10,189,023 B2* | 1/2019 | Glezer | G01N 33/6845 |
| 10,197,562 B2* | 2/2019 | Manuguerra | G01N 33/564 |
| 10,209,248 B2* | 2/2019 | Manuguerra | G02B 6/0016 |
| 10,352,930 B2* | 7/2019 | Manuguerra | G02B 6/0038 |
| 10,676,511 B2 | 6/2020 | Gershoni et al. | |
| 10,787,501 B1* | 9/2020 | Babb | A61K 39/15 |
| 10,844,442 B1 | 11/2020 | Barnhizer et al. | |
| 11,021,531 B1* | 6/2021 | Glanville | A61K 39/42 |
| 11,054,429 B1* | 7/2021 | Wang | C07K 14/165 |
| 11,105,804 B1* | 8/2021 | Huang | G01N 33/56983 |
| 11,112,412 B1* | 9/2021 | Wang | G01N 33/6854 |
| 11,130,994 B2* | 9/2021 | Shachar | G16H 50/80 |
| 11,249,083 B1* | 2/2022 | Huang | G01N 33/6845 |
| 11,255,855 B1* | 2/2022 | Huang | G01N 33/56983 |
| 11,345,741 B2* | 5/2022 | Crowe, Jr. | C07K 16/10 |
| 11,491,252 B1* | 11/2022 | Timme | A61L 2/26 |
| 2005/0037338 A1* | 2/2005 | Tseng | C12Q 1/701 435/5 |
| 2006/0188519 A1 | 8/2006 | Cheung et al. | |
| 2006/0188982 A1* | 8/2006 | Johnson | G01N 33/56983 435/6.1 |
| 2006/0240515 A1* | 10/2006 | Dimitrov | C07K 16/10 435/325 |
| 2006/0263847 A1* | 11/2006 | Siber | A61P 29/00 435/6.1 |
| 2006/0292651 A1* | 12/2006 | Juillerat | C12N 9/1085 435/15 |
| 2010/0009872 A1* | 1/2010 | Eid | G01N 33/54366 506/26 |
| 2014/0274762 A1* | 9/2014 | Manuguerra | G01N 33/564 506/18 |
| 2017/0089892 A1* | 3/2017 | Aghvanyan | G01N 33/54306 |
| 2017/0173128 A1* | 6/2017 | Hoge | A61K 39/39 |
| 2017/0336412 A1* | 11/2017 | Manuguerra | G02B 6/0038 |
| 2018/0016299 A1* | 1/2018 | Feigner | C12N 15/1086 |
| 2018/0038852 A1* | 2/2018 | Manuguerra | G02B 27/4272 |
| 2018/0172687 A1* | 6/2018 | Kaul | G01N 33/54326 |
| 2020/0300861 A1* | 9/2020 | Mena | G01N 33/6818 |
| 2021/0190797 A1* | 6/2021 | Messing | G01N 33/6857 |
| 2021/0246170 A1* | 8/2021 | Langedijk | C07K 14/005 |
| 2021/0292392 A1* | 9/2021 | Zhang | C07K 16/10 |
| 2021/0292393 A1* | 9/2021 | Westendorf | A61P 31/14 |
| 2021/0300999 A1* | 9/2021 | Crowe, Jr. | C07K 16/10 |
| 2021/0301295 A1* | 9/2021 | Fan | C12P 19/34 |
| 2021/0311055 A1* | 10/2021 | McDevitt | G01N 33/548 |
| 2021/0324048 A1* | 10/2021 | Walker | C07K 16/10 |
| 2021/0332110 A1* | 10/2021 | Nussenzweig | C07K 16/10 |
| 2021/0341468 A1* | 11/2021 | Hasegawa | G01N 33/553 |
| 2021/0347858 A1* | 11/2021 | Starzl | C07K 16/10 |
| 2021/0347860 A1* | 11/2021 | Emig | C07K 16/10 |
| 2021/0349105 A1* | 11/2021 | Walker | G01N 33/6854 |
| 2021/0356465 A1* | 11/2021 | Svarovsky | G01N 33/587 |
| 2021/0389308 A1* | 12/2021 | Lapointe | C07K 14/005 |
| 2021/0389322 A1* | 12/2021 | Tang | G01N 21/6428 |
| 2021/0403509 A1* | 12/2021 | Sleytr | C07K 14/32 |
| 2022/0042992 A1* | 2/2022 | Altin | A61K 39/12 |
| 2022/0056153 A1* | 2/2022 | Maddon | A61K 39/3955 |
| 2022/0098283 A1* | 3/2022 | Maddon | C07K 16/08 |
| 2022/0168414 A1* | 6/2022 | Cohen | A61K 39/215 |

FOREIGN PATENT DOCUMENTS

| | | |
|---|---|---|
| CN | 111303254 | 6/2020 |
| CN | 111474345 | 7/2020 |
| CN | 111505277 | 8/2020 |
| CN | 111521805 | 8/2020 |
| CN | 111537746 | 8/2020 |
| CN | 111551743 | 8/2020 |
| CN | 111978396 | 11/2020 |
| CN | 111978397 | 11/2020 |
| CN | 111978398 | 11/2020 |
| CN | 111978399 | 11/2020 |
| CN | 111995672 | 11/2020 |
| CN | 112010962 | 12/2020 |
| CN | 113295862 | 8/2021 |
| CN | 113295873 | 8/2021 |
| DE | 202020105116 | 11/2020 |
| EP | 1639374 | 3/2006 |
| WO | WO 2021/184391 | 9/2021 |
| WO | WO 2021/189058 | 9/2021 |
| WO | WO 2021/194826 | 9/2021 |
| WO | WO 2021/195136 | 9/2021 |

OTHER PUBLICATIONS

Korber, B et al. "Tracking Changes in SARS-CoV-2 Spike: Evidence that D614G Increases Infectivity of the COVID-19 Virus" *Cell*, Aug. 20, 2020, epub Jul. 3, 2020, pp. 812-827, vol. 182, No. 4, abstract only.

Berry, J. D. et al. "Neutralizing epitopes of the SARS-CoV S-protein cluster independent of repertoire, antigen structure or mAb technology" mAbs, Jan./Feb. 2010, pp. 53-66, vol. 2, Issue 1.

Zhu, Z et al. "Potent cross-reactive neutralization of SARS coronavirus isolates by human monoclonal antibodies" *PNAS*, Jul. 17, 2007, pp. 12123-12128, vol. 104, No. 29.

Koyama, T et al. "Variant analysis of SARS-CoV-2 genomes" *Bull World Health Organ.*, Jun. 2, 2020, pp. 495-504, vol. 98, No. 7.

* cited by examiner

1. Beads conjugated with S mutants

2. Serum incubates with ACE2 and then incubates with beads

3. If Ab binds to protein, ACE2 cannot binds to it (neutralization

IMMUNOASSAY FOR SARS-COV-2 NEUTRALIZING ANTIBODIES AND MATERIALS THEREFOR

CROSS-REFERENCE TO RELATED APPLICATIONS

This application claims the benefit of U.S. Provisional Application Ser. No. 63/053,888, filed Jul. 20, 2020, Ser. No. 63/088,195, filed Oct. 6, 2020 and Ser. No. 63/114,685, filed Nov. 17, 2020, the disclosures of which are hereby incorporated by reference in their entirety, including all figures, tables and amino acid or nucleic acid sequences.

The Sequence Listing for this application is labeled "Seq-List.txt" which was created on Jul. 15, 2021 and is 41 KB. The entire content of the sequence listing is incorporated herein by reference in its entirety.

BACKGROUND OF THE INVENTION

SARS-CoV-2, a coronavirus, is the causative viral agent of the disease COVID-19 which is a highly infectious human respiratory infection that threatens global public health. As of July 2020 this virus was known to have infected at least 10.2 million people worldwide with at least 502,000 known deaths.

Coronavirus (CoV) is an enveloped virus that contains a single-stranded positive-sense RNA. SARS-CoV-2, formerly known as 2019-nCoV, is a newly emerging coronavirus that mainly affects the respiratory tract that can lead to Severe Acute Respiratory Syndrome (SARS). The underlying disease caused by this virus is named COVID-19. Coronaviruses have been responsible for several outbreaks in the world during the two last decades. In 2003 and 2014, coronaviruses caused outbreaks mainly in Asia (SARS-CoV) and in the Middle East (MERS-CoV), respectively. Before the emergence of the new SARS-CoV-2, six coronaviruses were known to affect humans (SARS-CoV, MERS-CoV and four other coronaviruses that cause mild upper and lower respiratory syndromes).

SARS-CoV-2 was first identified in December 2019, in Wuhan City, Hubei Province, China, after several patients developed severe pneumonia similar to that caused by SARS-CoV. The virus has since rapidly spread around the globe and in March 2020, WHO officially announced COVID-19 as a pandemic. Person to-person transmission of the virus resulted in quick spreading of COVID-19 and the high number of patients requiring intensive care resulted in the establishment of containment measures. Individuals infected with COVID-19 exhibit disease symptoms about 2 to 14 days after infection.

The virus has been detected in respiratory secretions, which are considered as the primary means of transmission. Once viral particles enter the respiratory tract, the virus attaches to pulmonary cells via the ACE-2 receptors and are then endocytosed. SARS-CoV-2 can also be transmitted via the fecal route.

Patients positive for SARS-CoV-2 and that are symptomatic are diagnosed with COVID-19. Symptoms can vary drastically and notably include fever, dry cough, anosmia, sputum production, headaches, dyspnea, fatigue, nausea, and diarrhea. While some cases can be asymptomatic, others can lead to acute respiratory distress syndrome (ARDS) that is associated with a "cytokine storm" and even death.

Serological testing plays a critical role in understanding and combating the viral outbreaks. Serological testing can provide robust epidemiological data that are invaluable in determining the rates of infection and thus true mortality metrics. In addition, it can aid in determining individuals that mount a robust immune response who then can be donors for therapeutics agents, such as immune (convalescent) plasma. Serological testing can also help determine the immune response of asymptomatic individuals and/or vaccinated individuals.

The SARS-CoV-2 genome codes for four main structural proteins: spike (S), envelope (E), nucleoprotein (N) and membrane (M) proteins. The spike glycoproteins were found to bind to the ACE-2 receptors for entry into the cell. Studies indicate that IgG antibodies are primarily to the S and N proteins. The spike protein has two primary subunits: subunit 1 (S1) which includes the Receptor Binding Domain (RBD) that attaches the virus to the cell membrane, binding to the human ACE2 receptor. Subunit 2 (S2) mediates the fusion of the virus and cellular membranes.

A neutralizing antibody from infected or vaccinated individuals can block the binding between ACE2 receptor and spike proteins. However, it has been revealed that the viral spike proteins tend to mutate during its spread in the population which results in escape from neutralizing antibodies raised against the wild type spike protein, such as those that may be found in a vaccine. This invention identifies neutralizing antibody for multiple spike proteins capable of interacting with the ACE2 receptor.

BRIEF SUMMARY OF THE INVENTION

The present invention relates to the development of novel immunoassays for the detection of individuals infected by SARS-CoV-2 by detecting SARS-CoV-2 expressing spike protein variants and/or antibodies that neutralize SARS-CoV-2 spike protein variants. The immunoassays can be performed via a standard immunoassay format or on an automated platform. In various embodiments, the immunoassays use one or more SARS-CoV-2 spike protein variants or fragments thereof. The SARS-CoV-2 spike protein variants or fragments thereof can be immobilized on a substrate and used for the detection of neutralizing antibodies in biological samples obtained from subjects (also referred to as "patient samples"), optionally in combination with one or more cytokine in the biological sample. Other aspects of the invention provide antigen/substrate combinations for use in the immunoassays described herein.

The present invention also relates to the development of a novel singleplex and/or multiplex immunoassay for the detection of neutralizing and/or protective antibodies. A multiplex immunoassay can further detect high avidity neutralizing and/or protective antibodies, for SARS-CoV-2 spike protein variants or fragments thereof and, optionally, one or more cytokine selected from IL-1beta, IFN-γ, IFNγ-induced protein 10 (IP-10), and monocyte chemoattractant protein 1 (MCP-1), IL-4, IL-10, IL-2R, IL-6, granulocyte colony-stimulating factor (G-CSF), macrophage inflammatory protein-1A, and TNF-α in patient samples suspected of infection by the virus. The disclosed singleplex and/or multiplex immunoassays are designed to identify those subjects (patient samples) that contain antibodies capable of neutralizing and/or blocking the binding of the ACE2 receptor to a particular SARS-CoV-2 spike protein variants or fragment thereof and, optionally, levels of one or more cytokine in a patient infected by SARS-CoV, treated with an antibody that neutralizes SARS-CoV-2 spike protein variants or fragments thereof, or a subject immunized with a vaccine comprising a SARS-CoV2 spike protein, including the SARS-CoV-2 spike protein variants or fragments thereof disclosed herein, or a fragment thereof. The immunoassays disclosed herein can be used to evaluate the effectiveness of a vaccine against SARS-CoV-2 spike protein and variants thereof with respect to the generation of neutralizing antibodies and/or evaluate the presence of neutralizing antibodies in convalescent plasma or an antibody cocktail that is to be administered to a subject or at various time points after administration of convalescent plasma or an antibody cocktail comprising spike protein neutralizing antibodies to a subject.

DETAILED DESCRIPTION OF THE INVENTION

Figure 1:
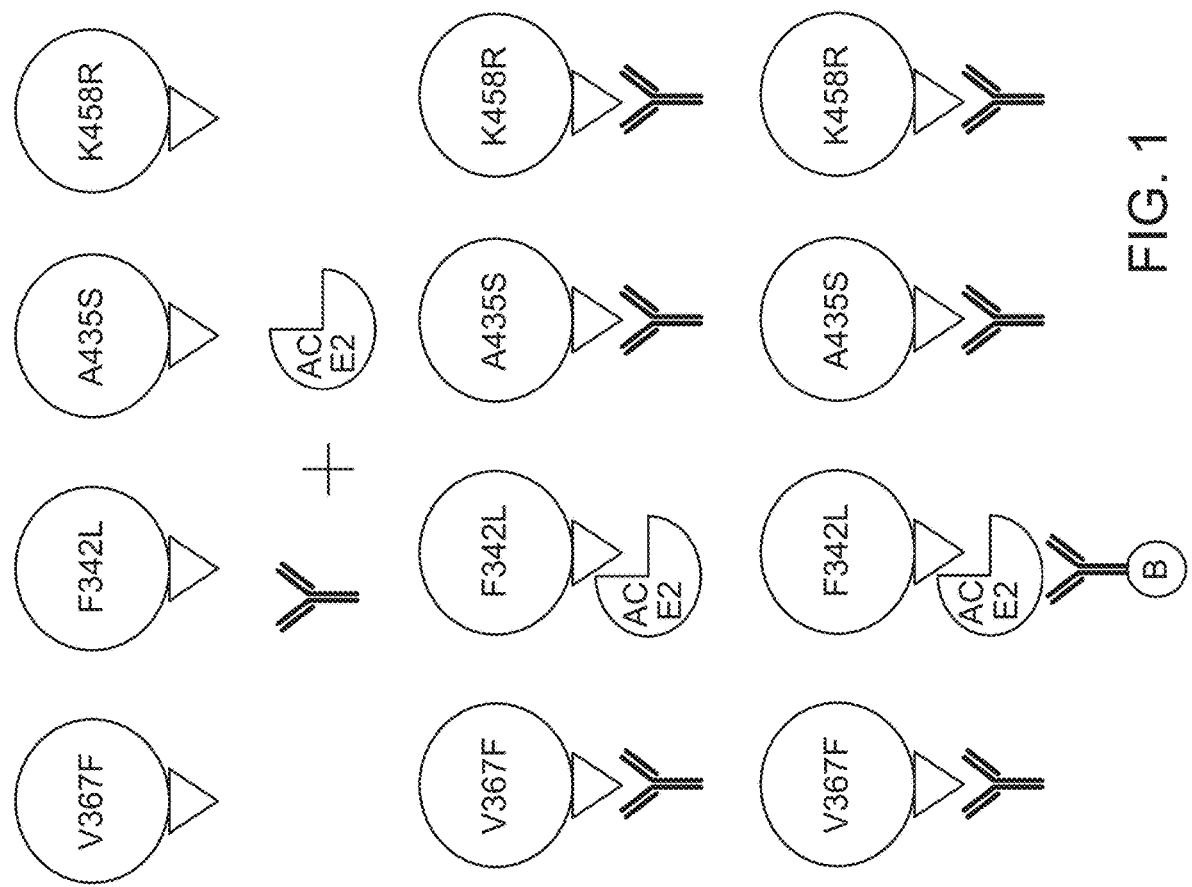
FIG. 1 illustrates one aspect of the invention in which neutralizing antibodies to SARS-CoV-2 spike protein variants or fragments thereof are identified.
Figure 2:
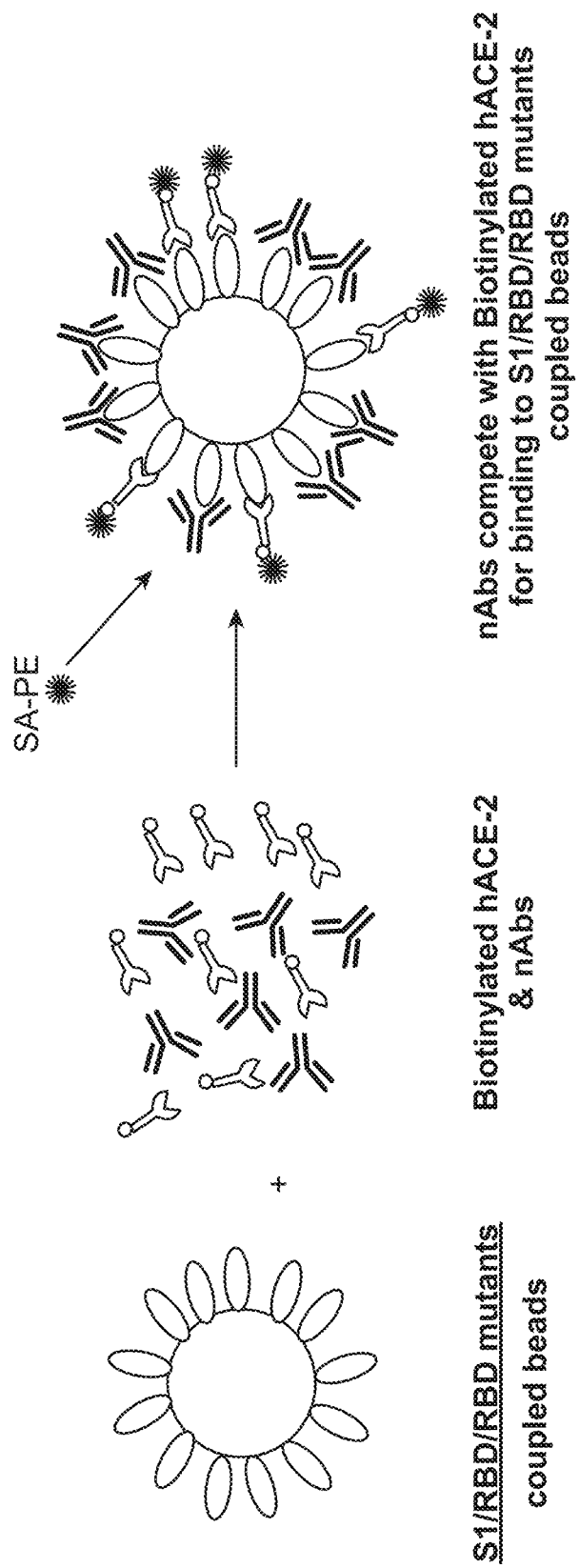
FIG. 2 illustrates one aspect of the invention in which neutralizing antibodies to SARS-CoV-2 spike protein variants or fragments thereof block the binding of hACE2 to SARS-CoV-2 spike protein variants or fragments thereof. The assay uses biotinylated hACE2 and streptavidin-phycoerythrin to permit detection of the neutralizing antibodies.
Figure 3:
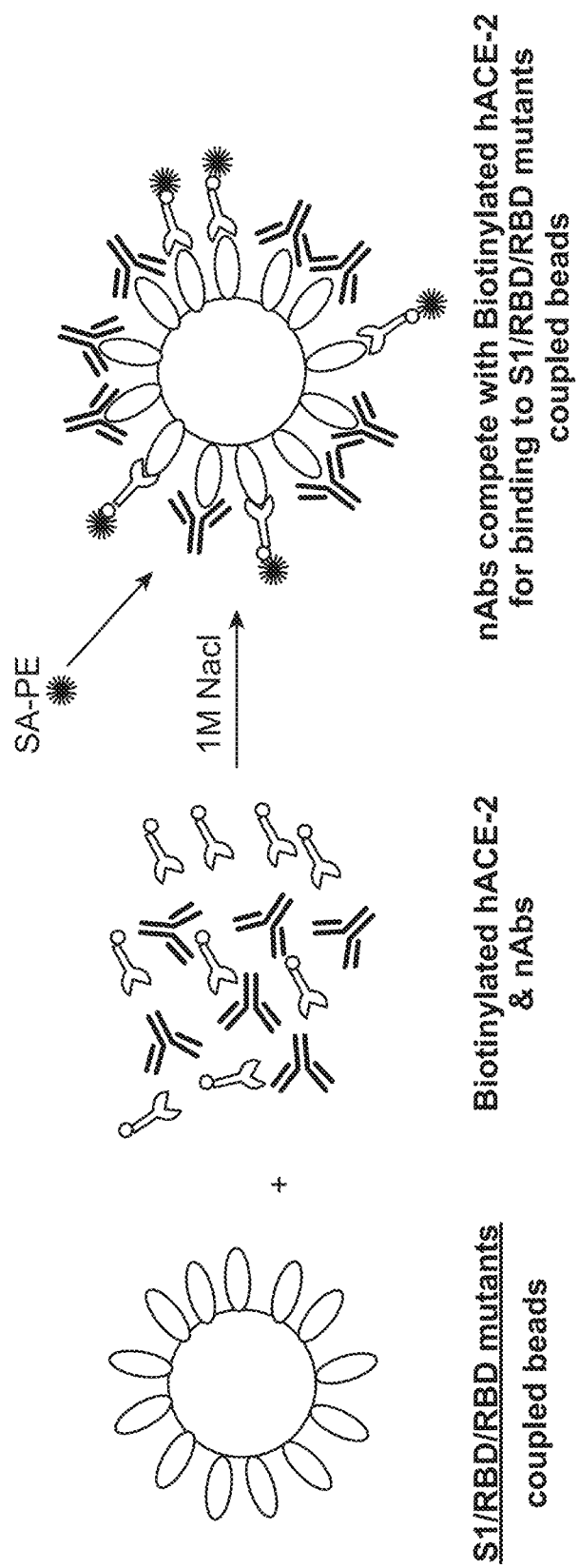
FIG. 3 illustrates one aspect of the invention in which high avidity neutralizing antibodies to SARS-CoV spike protein domains, variants, or fragments thereof are identified; the addition of 1 M NaCl destabilizes low avidity antibody binding.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value.

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values.

The present disclosure may refer to items, such as labels, solid supports, beads, analytes, etc. according to number or letter (e.g., Detectable label 1, bead (ii), etc.). Where this nomenclature is used, these numbers and letters are meant to distinguish the item from other items of the same type (e.g., bead (i) vs. bead (ii)), and are not meant to associate a specific property with the number or letter. Any methods, devices and materials similar or equivalent to those described herein can be used in the practice of this invention. The following definitions are provided to facilitate understanding of certain terms used frequently herein and are not meant to limit the scope of the present disclosure.

Multiplex assays are analyses that simultaneously measure the levels of more than one analyte in a single sample. Multiplex assay methods and reagents are described, e.g., in U.S. Pat. No. 6,872,578 and WO2008148883 (each of which is hereby incorporated by reference in its entirety). In the context of this application, the analytes to be measured are neutralizing and/or protective antibodies specific to the SARS-CoV-2 spike protein variants, or fragments thereof affixed to the solid substrates disclosed herein.

Singleplex assays are analyses that measure the level of one analyte in a single sample. In the context of this application, the analyte to be measured is a neutralizing and/or protective antibody specific to the SARS-CoV-2 spike protein or a fragment thereof or a SARS-CoV-2 spike protein variant or fragment thereof affixed to the solid substrates disclosed herein.

The term "solid support" or "substrate" (and grammatical equivalents of these terms) are used to denote a solid inert surface or body to which an agent, such as an antibody or a peptide or protein can be immobilized. These terms ("solid support" or "substrate" (and grammatical equivalents of these terms)) may be used interchangeably. Non-limiting examples of a solid support or substrate include plastic, polystyrenes, nitrocellulose, membranes, chips, and particles. If solid supports other than particles are used, for instance, glass, polymeric or silica chips (such as microchips), plates, slides, etc., the peptides and/or proteins (target analytes) disclosed herein can be immobilized on the surface of the support at specific locations (e.g., in specific wells of a plate (e.g., microtiter plate) or at specific locations on a chip, microchip, plate or slide). Thus, it is possible to differentiate neutralizing antibodies specific for spike protein variants within a sample by the location at which specific binding between antibodies in a sample and the spike protein variants, or fragments thereof occurs on the surface of the support.

Alternatively, lateral flow immunoassays can be performed in a manner analogous to those disclosed in U.S. Pat. Nos. 5,851,776 and 6,777,190 (each of which is hereby incorporated by reference in their entireties and which relate to lateral flow chromatographic assays on a membrane or other porous or non-porous materials). The specific binding of antibodies to the spike protein variants or fragments thereof that are immobilized at discrete locations on the membrane or other porous or non-porous material is then detected using conventional methods. The term "particle" is used herein to refer to a solid or semisolid body, often with linear dimensions on the micron scale (i.e., less than about 100 microns), of any shape or surface texture. Except as noted, the term is used interchangeably with "particle," which refers to a micron scale particle, and "bead," which refers to particles that are spherical or near-spherical in shape, often polymeric in composition. Where used in this application, the terms "particle" and "bead" (and grammatical equivalents of these terms) can be interchanged without altering the context of the passages within this application).

The term "immobilized" as used herein denotes a molecular-based coupling that is not significantly de-coupled under the conditions imposed during the steps of the assays described herein. Such immobilization can be achieved through a covalent bond, a non-covalent bond, an ionic bond, an affinity interaction (e.g., avidin-biotin or polyhistidine-$Ni^{++}$), or any other chemical bond.

Immobilization of the spike protein variants or fragments thereof disclosed in this application can be performed by covalent or non-covalent immobilization on a substrate. For example, non-covalent immobilization can be non-specific (e.g., non-specific binding of a combination of one or more spike protein variants or fragments thereof to a polystyrene surface). Specific or semi-specific binding to a substrate can be achieved by the spike protein variants or fragments thereof having a moiety that enables covalent or non-covalent binding of the peptide and/or protein to the substrate that is coated with a ligand that binds to the moiety. For example, the moiety can be a biotin or biotinyl group or an analogue thereof bound to an amino acid group of the spike protein variants or fragment thereof, such as 6-aminohexanoic acid, and the ligand (biotin binding ligand) is avidin, streptavidin or an analogue thereof. Alternatively, the moiety can be a His-His-His-His-His-His peptide and the substrate can be derivatized with a Nitrilotriacetic Acid derivative (NTA) charged with $Ni^{++}$ ions.

Various substrates suitable for use in the disclosed methods include, and are not limited to, magnetic beads, polystyrene beads, latex beads, beads comprising co-polymers, such as styrene-divinyl benzene; hydroxylated styrene-divinyl benzene; polystyrene; carboxylated polystyrene; carbon black; non-activated, polystyrene or polyvinyl chloride activated glass; or epoxy-activated porous magnetic glass. In other embodiments, the substrate can be the floor or wall of a microtiter well; a filter surface or membrane (e.g., a nitrocellulose membrane or a PVDF (polyvinylidene fluoride) membrane, such as an Immobilon membrane); a hollow fiber; a beaded chromatographic medium (e.g., an agarose or polyacrylamide gel); a magnetic bead; a fibrous cellulose matrix; an HPLC matrix; an FPLC matrix; or any other suitable carrier, support or surface. In one embodiment of the invention, the disclosed SARS-CoV-2 spike protein variants or fragments thereof are immobilized onto polystyrene beads (microspheres), wherein each protein is immobilized onto a bead with a unique detectable physical parameter, and are analyzed by a platform capable of distinguishing the detectable physical parameter. Such beads can, optionally, also contain a magnetic core. Such assays may be referred to as "multiplex immunoassays" and are discussed in detail below.

Devices for performing specific binding assays, especially immunoassays, are known and can be readily adapted for use in the present methods. Solid phase assays, in general, are easier to perform than heterogeneous assay methods which require a separation step, such as precipitation, centrifugation, filtration, chromatography, or magnetism, because separation of reagents is faster and simpler. Solid-phase assay devices include microtiter plates, flow-through assay devices, chips, microchips, lateral flow substrates dipsticks and immunocapillary or immunochromatographic immunoassay devices.

The terms "receptacle," "vessel," "tube," "well," etc. refer to a container that can hold reagents or an assay. If the receptacle is in a kit and holds reagents, it will typically be closed or sealed. If the receptacle is being used for an assay, it will typically be open or accessible during steps of the assay.

The terms "patient sample" or "biological sample" encompasses a variety of sample types obtained from an organism, such as a human. The term encompasses bodily fluids, such as blood, blood components, saliva, nasal mucous, serum, plasma, cerebro-spinal fluid (CSF), urine and other liquid samples of biological origin, solid tissue biopsy, tissue cultures, or supernatant taken from cultured patient cells. In the context of the present disclosure, the biological sample is typically a bodily fluid with detectable amounts of antibodies, e.g., blood or a blood component (e.g., plasma or serum) or a nasal secretion (mucous). The biological sample can be processed prior to assay, e.g., to remove cells or cellular debris. The term encompasses samples that have been manipulated after their procurement, such as by treatment with reagents, solubilization, sedimentation, or enrichment for certain components.

The term "antibody" as used herein refers to a polypeptide encoded by an immunoglobulin gene or immunoglobulin genes, or fragments thereof, which specifically bind and recognize an analyte (antigen). The recognized immunoglobulin light chains are classified as either kappa or lambda. Immunoglobulin heavy chains are classified as gamma, mu, alpha, delta, or epsilon, which in turn define the immunoglobulin classes, IgG, IgM, IgA, IgD and IgE, respectively. An example of a structural unit of immunoglobulin G (IgG antibody) is a tetramer. Each such tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains, respectively.

Antibodies exist as intact immunoglobulins or as well-characterized fragments produced by digestion of intact immunoglobulins with various peptidases. Thus, for example, pepsin digests an antibody near the disulfide linkages in the hinge region to produce $F(ab')_2$, a dimer of Fab which itself is a light chain joined to VH-CH1 by a disulfide bond. The $F(ab')_2$ dimer can be reduced under mild conditions to break the disulfide linkage in the hinge region, thereby converting the $F(ab')_2$ dimer into two Fab' monomers. The Fab' monomer is essentially an Fab with part of the hinge region (see, Paul (Ed.), Fundamental Immunology, Third Edition, Raven Press, N.Y. (1993)). While various antibody fragments are defined in terms of the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies.

Antibodies are commonly referred to according their targets. While the nomenclature varies, one of skill in the art will be familiar and understand that several names can be applied to the same antibody. For example, an antibody specific for IgM can be called "anti-IgM," "IgM antibody," "anti-IgM antibody," etc.

The terms "specific for," "specific to", "specifically binds," and grammatically equivalent terms refer to a molecule (e.g., antibody or antibody fragment) that binds to its target with at least 2-fold greater affinity than non-target compounds, e.g., at least any of 4-fold, 5-fold, 6-fold, 7-fold, 8-fold, 9-fold, 10-fold, 20-fold, 25-fold, 50-fold, or 100-fold greater affinity. For example, antibodies that specifically binds a given antibody target will typically bind the antibody target with at least a 2-fold greater affinity than a non-antibody target. Specificity can be determined using standard methods, e.g., solid-phase ELISA immunoassays (see, e.g., Harlow & Lane, *Using Antibodies, A Laboratory Manual* (1998) for a description of immunoassay formats and conditions that can be used to determine specific immunoreactivity).

The term "binds" with respect to an antibody target (e.g., antigen, analyte), typically indicates that an antibody binds a majority of the antibody targets in a pure population (assuming appropriate molar ratios). For example, an antibody that binds a given antibody target typically binds to at least %3 of the antibody targets in a solution (e.g., at least any of 75, 80, 85, 90, 91, 92, 93, 94, 95, 96, 97, 98, 99, or 100%). One of skill will recognize that some variability will arise depending on the method and/or threshold of determining binding.

The terms "label," "detectable label," "detectable moiety," and like terms refer to a composition detectable by spectroscopic, photochemical, biochemical, immunochemical, chemical, or other physical means. For example, useful labels include fluorescent dyes (fluorophores), luminescent agents, electron-dense reagents, enzymes (e.g., as commonly used in an ELISA), biotin, enzymes acting on a substrate (e.g., horseradish peroxidase), digoxigenin, $^{32}P$ and other isotopes, haptens, and proteins which can be made detectable, e.g., by incorporating a radiolabel into the peptide or used to detect antibodies specifically reactive with the peptide. The term includes combinations of single labeling agents, e.g., a combination of fluorophores that provides a unique detectable signature, e.g., at a particular wavelength or combination of wavelengths. Any method known in the art for conjugating label to a desired agent may be employed, e.g., using methods described in Hermanson, *Bioconjugate Techniques* 1996, Academic Press, Inc., San Diego.

The term "positive," when referring to a result or signal, indicates the presence of an analyte or item that is being detected in a sample. The term "negative," when referring to a result or signal, indicates the absence of an analyte or item that is being detected in a sample. Positive and negative are typically determined by comparison to at least one control, e.g., a threshold level that is required for a sample to be determined positive, or a negative control (e.g., a known blank). A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. For the assays used in the subject invention, control beads can be included, for example, a serum verification bead (SVB) and/or an internal standard bead (ISB) can be used. One of skill in the art will recognize that controls can be designed for assessment of any number of parameters, and will understand which controls are valuable in a given situation and be able to analyze data based on comparisons to control values. Controls are also valuable for determining the significance of data. For example, if values for a given parameter are variable in controls, variation in test samples will not be considered as significant.

A "calibration control" is similar to a positive control, in that it includes a known amount of a known analyte. In the case of a multiplex assay, the calibration control can be designed to include known amounts of multiple known analytes. The amount of analyte(s) in the calibration control can be set at a minimum cut-off amount, e.g., so that a higher amount will be considered "positive" for the analyte(s), while a lower amount will be considered "negative" for the analyte(s). In some cases, multilevel calibration controls can be used, so that a range of analyte amounts can be more accurately determined. For example, an assay can include calibration controls at known low and high amounts, or known minimal, intermediate, and maximal amounts.

The term "diagnosis" refers to a relative probability that a subject has an infection, disorder or disease. Similarly, the term "prognosis" refers to a relative probability that a certain future outcome may occur in the subject. For example, in the context of the present disclosure, prognosis can refer to the likelihood that an individual has been infected by SARS-CoV-2 and has, or will develop, disease. The terms are not intended to be absolute, as will be appreciated by any one of skill in the field of medical diagnostics.

"Subject," "patient," "individual" and grammatical equivalents thereof are used interchangeably and refer to, except where indicated, mammals, such as humans and non-human primates, as well as rabbits, felines, canines, rats, mice, squirrels, goats, pigs, deer, and other mammalian species. The term does not necessarily indicate that the subject has been diagnosed with a particular disease, but typically refers to an individual under medical or veterinary supervision. A patient can be an individual that is seeking treatment, monitoring, adjustment or modification of an existing therapeutic regimen, etc. In the context of this application, the "subject," "patient," or "individual" has: a) been exposed to or infected with SARS-CoV-2; b) immunized with a vaccine comprising the SARS-CoV-2 spike protein (or fragments thereof) or a vaccine comprising spike protein variants or fragments thereof; or c) been treated with a neutralizing antibody for the SARS-CoV-2 spike protein (or fragments thereof) or with neutralizing antibody specific for SARS-CoV-2 spike protein variants or fragments thereof (e.g., convalescent plasma or other neutralizing antibody, such as a composition comprising one or more antibodies that neutralize the SARS-CoV-2 spike protein or variants thereof (an antibody cocktail). The immunoassays disclosed herein are capable of detecting the binding of neutralizing antibodies for specific for SARS-CoV-2 spike protein variants or fragments thereof in biological samples from any of these types of subjects.

As used herein, a "chaotropic agent" or "chaotrop" refers to a chemical compound that destabilizes the three-dimensional structure of proteins. In certain embodiments, a chaotropic agent may refer to an ionic chaotrop (e.g., a chaotropic ion or a chaotropic salt) or, alternatively, to a nonionic chaotrop. Non-limiting examples of chaotropic salts include: guanidinium salts, e.g., guanidinium chloride, guanidinium nitrate, guanidinium thiocyanate; thiocyanate salts, e.g., ammonium thiocyanate, potassium thiocyanate, sodium thiocyanate, lithium thiocyanate, calcium thiocyanate, guanidinium thiocyanate; perchlorate salts, e.g., ammonium perchlorate, sodium perchlorate, lithium perchlorate, magnesium perchlorate, calcium perchlorate; iodate salts, e.g., ammonium iodate, potassium iodate, sodium iodate, lithium iodate, magnesium iodate, calcium iodate; chlorate salts, e.g., sodium chlorate, lithium chlorate, magnesium chlorate, calcium chlorate; chloride salts, e.g., sodium chloride, potassium chloride, calcium, chloride, and ammonium chloride. Nonionic chaotropes include, without limitation, urea and thiourea.

As used herein, "avidity" is a measure of the total binding strength of an antigen comprising various antigenic determinants and antibodies, i.e., the stability of the complex formed between the antigen and the antibody. Avidity refers to the total binding force between antigens and antibodies; therefore, the phrases "high avidity antibody" or "low avidity antibody" reflect the relative binding force of an antibody to an antigen. As used herein, a high avidity antibody can maintain a bond to an antigen when exposed to a chaotropic agent; while, a low avidity antibody may not be able to maintain a bond to an antigen when exposed to same chaotropic agent at the same concentration.

The term "ACE2 receptor(s)" (ACE2R) includes truncated and/or modified ACE2 receptors that can have one, two, three, four, five, ten, 50, 100, 250, 500 or more amino acids removed, added, and/or substituted. A modified ACE2 receptor includes an ACE2 receptor fusion protein in which the ACE2 receptor, or a fragment or variant thereof is fused to an immunoglobulin Fc domain. For example, the Fc domain can be fused to the C-terminus of the ACE2 receptor, or a fragment or variant of the ACE2 receptor to form an ACE2R-Fc fusion protein. The fragment or variant of the ACE2 receptor can comprise a minimal domain from ACE2R that is sufficient to bind to the RBD, for example amino acids Ser19-Asp615 of ACE2R or amino acids 12-327 of the ACE2R. In various embodiments, human ACE2R (SEQ ID NO: 4) can be used. A "labeled ACE2 receptor" includes an ACE2 receptor that is detectably labeled (for example, with PE) or is a biotinylated, avidinated, or streptavidinated ACE2 receptor (including truncated and/or modified ACE2 receptors or ACE2 fusion proteins). In various embodiments, ACE2R-Fc fusion proteins can be biotinylated, avidinated, or streptavidinated on the Fc portion of the fusion protein.

The terms "structural protein" "peptide", "antigen", "analyte", and "fragment" (and grammatical equivalents thereof) can be used interchangeably and refer to the disclosed SARS-CoV-2 spike protein variants or fragments thereof that are disclosed herein and/or the unmutated SARS-CoV-2 spike protein or fragments thereof (SEQ ID NO: 3). As discussed herein, fragments of the disclosed SARS-CoV-2 spike protein, SARS-CoV-2 spike protein variants are between 5 and (n–1) consecutive amino acids of a given SARS-CoV-2 spike protein (SEQ ID NO: 1 or SEQ ID NO: 2 or SEQ ID NO: 3). In each instance, a fragment of the spike protein variant will include, within its span of consecutive amino acids, the amino acid mutation associated with the mutant spike protein (which are identified in Table 1 and Table 2). The numbering of the amino acid mutation is in relation to the amino acid numbering in SEQ ID NOs: 1 or 2.

TABLE 1

Spike protein variants

| Protein | Amino acid mutation | aa range | AA substitution |
|---|---|---|---|
| S1 | 367 | 319-541 | Any amino acid, preferably F, L, A, V, I, M, Y or W |
| S1 | 342 | 319-541 | Any amino acid, preferably L, A, V, I, M. F, Y or W |
| S1 | 435 | 319-541 | Any amino acid, preferably S, T, N or Q |
| S1 | 458 | 319-541 | Any amino acid, preferably R, H or K |
| S1 | 483 | 319-541 | Any amino acid, preferably A, L, V, I, M, F, Y or W |
| S1 | 354 | 319-541 | Any amino acid, preferably D or E |
| S1/S2 | 683, 685, 986, and/or 987 | 1-1213 | Any amino acid, preferably L, A, V, I, M, F, Y, G, P or W |

TABLE 2

Preferred Spike protein variants

| Protein | Mutant Type | AA Range | ACE2 Binding |
|---|---|---|---|
| S1 | V367F | aa 319-541 | + |
| S1 | F342L | aa 319-541 | + |
| S1 | A435S | aa 319-541 | + |
| S1 | K458R | aa 319-541 | + |
| S1 | V483A | aa 319-541 | + |
| S1 | N354D | aa 319-541 | + |
| S1/S2 | R683A, R685A, K986P, V987P | aa 1-1213 | + |

With respect to the amino acid mutations at positions 683, 685, 986, and 987, any combination of 2, 3 or 4 amino acid mutations can exist in the spike protein variant or a fragment thereof. In certain embodiments, three or all four amino acid mutations exist within the spike protein variant or fragment thereof. Thus, fragments of the spike protein variants that can be immobilized on a solid support are fragments of S1 and can be between 5 and 685 consecutive amino acids in length, provided that the fragment includes one or more of the amino acid substitutions identified in Table 1 or 2 (for example, amino acids 13-685 or amino acids 319-541 of SEQ ID NO: 1 or 2). Preferred embodiments provide for spike protein variants, or fragments thereof, that contain a single amino acid substitution as identified in Tables 1 and 2. The length or a fragment can include or exclude signal peptides that are processed (for example amino acids 1-12 of SEQ ID NO: 1 or SEQ ID NO: 2). In some embodiments, the amino acid at position 354 of SEQ ID NO. 2 is Asx (aspartic acid or asparagine). Spike protein variants of SEQ ID NO: 2, thus, can contain either aspartic acid or asparagine at position 354 and one or more other mutations identified in Tables 1 and 2 (i.e., at positions 342, 367, 435, 458, 483, 683, 685, 986, and/or 987). Thus, in the case of the spike protein variants, the length can include or exclude the signal peptide of the protein. In some embodiments, an "analyte" may be a neutralizing antibody specific for a SARS-CoV-2 spike protein variant or fragment thereof. In such embodiments, the use of the term in the context of detecting the antibody as the analyte will be clear. In yet other embodiments, one or more of the following chemokines and cytokines are included as an "analyte" or "analytes" that are to be detected and/or quantified: IL-1beta, IFN-γ, IFNγ-induced protein 10 (IP-10), and monocyte chemoattractant protein 1 (MCP-1), IL-4, IL-10, IL-2R, IL-6, granulocyte colony-stimulating factor (G-CSF), macrophage inflammatory protein-1A, and TNF-α. While IL-1beta, IFN-γ, IFN-γ-induced protein 10 (IP-10), and monocyte chemoattractant protein 1 (MCP-1), IL-4, IL-10, IL-2R, IL-6, granulocyte colony-stimulating factor (G-CSF), macrophage inflammatory protein-1A, and TNF-α are either classified as cytokines or chemokines (in the case of IP-10), this collection of cytokines and chemokines (IL-1beta, IFN-γ, IFN-γ-induced protein 10 (IP-10), and monocyte chemoattractant protein 1 (MCP-1), IL-4, IL-10, IL-2R, IL-6, granulocyte colony-stimulating factor (G-CSF), macrophage inflammatory protein-1A, and TNF-α) can be referred to herein as "cytokines" "cytokine", or "one or more cytokine". As discussed above, the use of the term in the context of detecting or immobilizing these chemokines and/or cytokines ("cytokines", "cytokine", or "one or more cytokine") will be clear.

As discussed above, the present invention relates to the development of a novel multiplex immunoassay for the detection of neutralizing antibodies for SARS-CoV-2 spike protein variants or fragments thereof and, optionally, one or more cytokine selected from IL-1beta, IFN-γ, IFN-γ-induced protein 10 (IP-10), and monocyte chemoattractant protein 1 (MCP-1), IL-4, IL-10, IL-2R, IL-6, granulocyte colony-stimulating factor (G-CSF), macrophage inflammatory protein-1A, and TNF-α in patient samples suspected of infection by the virus. The disclosed immunoassays are designed to identify those subjects (patient samples) that contain antibodies capable of blocking the binding of the ACE2 receptor to a particular SARS-CoV-2 spike protein variants or fragment thereof and, optionally, levels of one or more cytokine in a patient or a subject immunized with a vaccine comprising SARS-CoV2 spike protein, or a fragment thereof. The immunoassay can be performed via a standard immunoassay using ELISA, lateral flow, magnetic assays with manual or using automated platforms. Particularly, the disclosed immunoassay uses one or more SARS-CoV-2 spike protein variant or fragment thereof that contains an amino acid substitution and any combination of the disclosed SARS-CoV-2 spike protein variants (e.g., any combination of two, three, four, five, six, seven, eight, or nine SARS-CoV-2 spike protein variants) and, optionally, one or more cytokine selected from IL-1beta, IFN-γ, IFNγ-induced protein 10 (IP-10), monocyte chemoattractant protein 1 (MCP-1), IL-4, IL-10, IL-2R, IL-6, granulocyte colony-stimulating factor (G-CSF), macrophage inflammatory protein-1A, and TNF-α (e.g., any combination of one, two, three, four, five, six, seven, eight, nine, ten, or eleven of these analytes).

Another embodiment provides an immunoassay in which a single SARS-CoV-2 spike protein variant or fragment thereof is immobilized on a substrate. Thus, the disclosed immunoassay comprises contacting a substrate to which a SARS-CoV-2 spike protein variant or fragment thereof has been immobilized under conditions effective to bind antibodies found in a biological sample to the immobilized SARS-CoV-2 spike protein variant or fragment thereof. Antibodies bound to the SARS-CoV-2 spike protein variant or fragment thereof that is attached to a substrate can then be detected by a species specific anti-IgM, anti-IgG, anti-IgA, anti-IgD, anti-IgE, anti-kappa, or anti-lambda antibody that is labeled (e.g., anti-human, anti-rabbit, anti-canine, anti-rat, anti-mouse, anti-squirrel, anti-goat, anti-pig or anti-deer antibody). For example, anti-IgG-PE and/or anti-IgM-PE reporters can be used to detect and/or quantify the SARS-CoV-2 spike protein variant specific antibodies in biological samples obtained from individuals suspected of infection by the virus or immunized with a vaccine comprising the SARS-CoV2 spike protein. Alternatively, it is possible to utilize species specific light chain specific antibodies (species specific kappa or lambda specific antibodies) as a detection reagent to identify samples containing antibodies that bind to a given SARS-CoV-2 spike protein variant or fragment thereof. In certain preferred embodiments, the species specific antibodies are anti-human antibodies.

Other embodiments provide for the use of labeled ACE2 receptor, including truncated and/or modified ACE2 receptors and/or ACE2R-fusion proteins (e.g., ACE2R-Fc fusion proteins) that are labeled, to detect substrates to which SARS-CoV-2 spike protein variants or fragments thereof are immobilized and to which a neutralizing antibody has not bound. The truncated and/or modified ACE2 receptor can have one, two, three, four, five, ten, 50, 100, 250, 500 or more amino acids removed, added, and/or substituted. Alternatively, the ACE2 receptor can be fused to an immunoglobulin Fc domain. For example, the Fc domain can be fused to the C-terminus of ACE2R, or a fragment or variant of the ACE2 receptor protein. The fragment or variant of the ACE2 receptor can comprise a minimal domain from ACE2R that is sufficient to bind to the RBD. Additionally, the ACE2 receptor, truncated or modified ACE2 receptor or an ACE2R fusion protein (e.g., ACE2R-Fc) can be biotinylated or avidinated. In preferred embodiments, the Fc domain of an ACE2R-Fc fusion protein can be biotinylated or avidinated. In such embodiments, it is possible to identify the binding of neutralizing antibody to a given SARS-CoV-2 spike protein variant or fragment thereof by the lack of labeled ACE2 receptor binding to a substrate to which a SARS-CoV-2 spike protein variant or fragment thereof has been immobilized. In other words, a labeled ACE2 receptor will only bind to those substrates to which no neutralizing antibodies are specifically bound by a SARS-CoV-2 spike protein variant or fragment thereof that is immobilized on a substrate.

The SARS-CoV-2 spike protein variant or fragment thereof disclosed herein can be immobilized on a solid support via covalent or non-covalent bonding. In embodiments where a SARS-CoV-2 spike protein variant or fragment thereof or cytokine is covalently immobilized on the substrate, carboxylated substrates, such as particles, plastics, polystyrenes or beads, are activated and esterified before adding the SARS-CoV-2 spike protein variant or fragment thereof or cytokine. Carboxyl activation is achieved using a water soluble carbodiimide, such as 1-cyclohexyl-3-(2-morpholinoethyl) carbodiimide (CMC). Esterification is achieved using NHS, NHSS or HOBt or other suitable reagents. After carboxyl activation and esterification, the SARS-CoV-2 spike protein variant or fragment thereof or cytokine are added to the activated surface in buffers with pH between 6-10 (an example of which is sodium acetate buffer pH 5.1, phosphate buffer pH 7.0 with or without detergent (e.g., CHAPS)). After the coupling, the substrate (e.g., beads) is blocked in buffers containing protein blockers, such as BSA, mouse IgG, bovine gamma globulin (BGG) or animal serum (goat, horse, murine). The protein blocker(s) can be present in an amount ranging from 0.1-10 weight/volume percent. The blocked antigen coupled substrates can then be washed with an appropriate buffer and used in a desired immunoassay format.

As discussed above, the disclosed invention is directed to an immunoassay which includes taking a sample of body fluid or tissue (e.g., a biological sample or a patient sample) likely to contain antibodies; contacting (reacting) the biological sample with a SARS-CoV-2 spike protein variant or fragment thereof (and/or one or more cytokine) under conditions effective for the formation of a specific protein-antibody complex (sometimes referred to as specific binding of the protein and the antibody or "an immunocomplex" of a given protein and antibodies that specifically bind the protein or fragment thereof); and assaying the contacted (reacted) sample for the presence of an antibody-analyte immunocomplex. The biological sample can be obtained from a SARS-CoV2 infected individual, an individual treated with neutralizing antibodies specific for SARS-CoV-2 spike protein variants or fragments, or an individual vaccinated with a vaccine comprising SARS-CoV2 spike protein.

In various embodiments, the disclosed method relates to a method that comprises taking a sample of body fluid or tissue (a biological sample or a patient sample) likely to contain antibodies specific for a SARS-CoV-2 spike protein variant or fragment thereof and detecting and/or quantifying the presence of the antibodies and/or one or more cytokine within the biological sample. Generally, IgM, IgA, and/or IgG antibodies are detected (although antibodies of other isotypes may also be detected). Alternatively, antibodies specific for kappa or lambda light chains can be used to detect antibodies specifically bound to the SARS-CoV-2 spike protein variant or fragment thereof or cytokine that is immobilized on a substrate. In various embodiments, the biological sample is a serum or plasma sample derived from a venous blood sample. Other body fluids, such as saliva, gastric secretions, nasal secretions, mucus, etc., that are known to contain antibodies may also be referred to as a biological sample and used in the disclosed immunoassays. As discussed above, the biological sample can be obtained from a SARS-CoV2 infected individual, an individual treated with neutralizing antibodies specific for SARS-CoV-2 spike protein variants or fragments or an individual vaccinated with a vaccine comprising SARS-CoV2 spike protein, such as a spike protein variant or fragment thereof as disclosed herein.

The presently described multiplex assays involve use of a solid support, typically particles or beads. For detection by flow cytometry, particles or beads that emit high levels of autofluorescence should be avoided since this will increase background signal and potentially render them unsuitable. Particles or beads created by standard emulsion polymerization from a variety of starting monomers generally exhibit low autofluorescence, while those that have been modified to increase porosity ("macroporous" particles) exhibit high autofluorescence. Autofluorescence in such particles or beads further increases with increasing size and increasing percentage of divinylbenzene monomer. Within these limitations, the size range of the particles or beads can vary and particular size ranges are not critical. In most cases, the aggregated size range of the particles or beads lies within the range of from about 0.3 micrometer to about 100 micrometers in particle or bead diameter, e.g., within the range of from about 0.5 micrometer to about 40 micrometers.

Magnetic particles or beads are commonly used in the art, and can make separation and wash steps more convenient for the presently described assays. "Magnetic particles," "magnetically responsive material," "magnetic beads," and like terms denote a material that responds to a magnetic field. Magnetically responsive materials include paramagnetic materials (e.g., iron, nickel, and cobalt, as well as metal oxides, such as $Fe_3O_4$, $BaFe_{12}O_{19}$, CoO, NiO, $Mn_2O_3$, $Cr_2O_3$, and CoMnP), ferromagnetic materials, ferrimagnetic materials, and metamagnetic materials. Rather than constituting the entire particle or bead, the magnetically responsive material typically constitutes one component of the microparticle or bead, while the remainder consists of a polymeric material which can be chemically derivatized to permit attachment of an assay reagent (e.g., antigen/analyte or antibody). Methods of, and instrumentation for, applying and removing a magnetic field as part of an assay are known to those skilled in the art and reported in the literature. Examples of literature reports are Forrest et al., U.S. Pat. No. 4,141,687; Ithakissios, U.S. Pat. No. 4,115,534; Vlieger et al., *Analytical Biochemistry* 205:1-7 (1992); Dudley, *Journal of Clinical Immunoassay* 14:77-82 (1991); and Smart, *Journal of Clinical Immunoassay* 15:246-251 (1992).

The polymeric matrix that forms the microparticle or bead can be any material that is compatible with the presently described multiplex assay. The matrix should be inert to the components of the biological sample and to the assay reagents, have minimal autofluorescence, be solid and insoluble in the sample and in any other reagents or washes used in the assay, and capable of affixing an assay reagent to the microparticle. Examples of suitable polymers are polyesters, polyethers, polyolefins, polyalkylene oxides, polyamides, polyurethanes, polysaccharides, celluloses, and polyisoprenes. Crosslinking is useful in many polymers for imparting structural integrity and rigidity to the microparticle.

Functional groups for attachment of the assay reagent (e.g., antigen/analyte or antibody) can be incorporated into the polymer structure by conventional means. Examples of suitable functional groups are amine groups, ammonium groups, hydroxyl groups, carboxylic acid groups, and isocyanate groups. The assay reagent is typically covalently bound to the solid phase surface, either directly or indirectly, e.g., with a linking group. Linking groups can be used as a means of increasing the density of reactive groups on the solid phase surface and decreasing steric hindrance to increase the range and sensitivity of the assay, or as a means of adding specific types of reactive groups to the solid phase surface to broaden the range of types of assay reagents that can be affixed to the solid phase. Examples of suitable useful linking groups are polylysine, polyglycine, polyaspartic acid, polyglutamic acid and polyarginine.

Particles or beads of different types in a multiplex assay can be distinguished from one another, e.g., by size, weight, light scatter or absorbance, reflectance, shape, or label, e.g., fluorescent (dye) label. Where particle or bead size is used as a differentiation factor (distinguishing characteristic), the widths of the size subranges and the spacing between mean diameters of adjacent subranges are selected to permit differentiation of different types of particles or beads by flow cytometry, as will be apparent to those skilled in the use of and instrumentation for flow cytometry. Typically, a subrange for a given mean diameter is about ±5% CV or less of the mean diameter, where CV is the coefficient of variation and is defined as the standard deviation of the particle or bead diameter divided by the mean particle diameter times 100 percent. The mean diameters of subranges for different types of particles are generally spaced apart by at least about 6% of the mean diameter of one of the subranges, e.g., at least about 8% or 10% of the mean diameter of one of the subranges.

Light scatter can also be used to distinguish different types of particles or beads. Side angle light scatter varies with particle or beads size, granularity, absorbance and surface roughness, while forward angle light scatter is mainly affected by size and refractive index. Varying any of these qualities can result in light scatter differences that can serve as a means of distinguishing the various groups of particles or beads.

Still another example of a differentiation parameter is absorbance. When light is applied to particles or beads, the absorbance of the light by the particles or beads is indicated mostly by a change in the strength of the laterally (side-angle) scattered light while the strength of the forward-scattered light is relatively unaffected. Consequently, the difference in absorbance between various colored dyes associated with the particles or beads is determined by observing differences in the strength of the laterally scattered light.

Other physical parameters that can be used as differentiation parameters to distinguish the particles or beads of one group from those of another include excitable fluorescent dyes or colored dyes that impart different emission spectra and/or scattering characteristics to the particles or beads. Alternatively, different concentrations of one or more fluorescent dyes can be used for distinguishing or differentiating particles or beads.

When the distinguishable characteristic is a fluorescent dye or color, it can be coated on the surface of the particle or bead, embedded in the particle or bead, or bound to the molecules of the particle or bead material. Thus, fluorescent particles or beads can be manufactured by combining the polymer material with the fluorescent dye, or by impregnating the particle or bead with the dye. Particles or beads with dyes already incorporated and thereby suitable for use in the present invention are commercially available, from suppliers, such as Spherotech, Inc. (Libertyville, Ill., USA) and Molecular Probes, Inc. (Eugene, Oreg., USA).

Labels can be any substance or component that directly or indirectly emits or generates a detectable signal. In some embodiments, the labels are fluorophores, many of which are reported in the literature and thus known to those skilled in the art, and many of which are readily commercially available. Literature sources for fluorophores include Cardullo et al., *Proc. Natl. Acad. Sci. USA* 85: 8790-8794 (1988); Dexter, *J. of Chemical Physics* 21: 836-850 (1953); Hochstrasser et al., *Biophysical Chemistry* 45: 133-141 (1992); Selvin, *Methods in Enzymology* 246: 300-334 (1995); Steinberg, *Ann. Rev. Biochem.*, 40: 83-114 (1971); Stryer, *Ann. Rev. Biochem.* 47: 819-846 (1978); Wang et al., *Tetrahedron Letters* 31: 6493-6496 (1990); and Wang et al., *Anal. Chem.* 67: 1197-1203 (1995). The following are non-limiting examples of fluorophores that can be used as labels:

4-acetamido-4'-isothiocyanatostilbene-2,2'disulfonic acid; acridine; acridine isothiocyanate; 5-(2'-aminoethyl) aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin; 7-amino-4-methylcoumarin (AMC, Coumarin 120); 7-amino-4-trifluoromethylcoumarin (Coumaran 151); cyanine dyes; cyanosine; 4',6-diaminidino-2-phenylindole (DAPI); 5',5''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansylchloride); 4-(4'-dimethylaminophenylazo)benzoic acid (DABCYL); 4-dimethylaminophenylazophenyl-4'-isothiocyanate (DABITC); eosin; eosin isothiocyanate; erythrosin B; erythrosin isothiocyanate; ethidium; 5-carboxyfluorescein (FAM); 5-(4,6-dichlorotriazin-2-yl)aminofluorescein (DTAF); 2',7'-dimethoxy-4'5'-dichloro-6-carboxyfluorescein (JOE); fluorescein; fluorescein isothiocyanate; fluorescamine; IR144; IR1446; Malachite Green isothiocyanate; 4-methylumbelliferone; ortho cresolphthalein; nitrotyrosine; pararosaniline; Phenol Red; phycoerythrin ((PE) including but not limited to B and R types); o-phthaldialdehyde; pyrene; pyrene butyrate; succinimidyl 1-pyrene butyrate; quantum dots; Reactive Red 4 (Cibacron™ Brilliant Red 3B-A); 6-carboxy-X-rhodamine (ROX); 6-carboxyrhodamine (R6G); lissamine rhodamine B sulfonyl chloride rhodamine; rhodamine B; rhodamine 123; rhodamine X isothiocyanate; sulforhodamine B; sulforhodamine 101; sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; and lanthanide chelate derivatives.

Particular fluorophores for use in the disclosed immunoassays include fluorescein, fluorescein isothiocyanate, phycoerythrin (PE), rhodamine B, and Texas Red (sulfonyl chloride derivative of sulforhodamine 101). Any of the fluorophores in the list preceding this paragraph can be used in the presently described assays, either to label the particle or bead, or to label a binding agent (e.g., an antibody or streptavidin). Fluorochromes can be attached by conventional covalent bonding, using appropriate functional groups on the fluorophores and on the particle or bead or binding agent (e.g., an antibody or streptavidin). The recognition of such groups and the reactions to form the linkages will be readily apparent to those skilled in the art. Other labels that can be used in place of the fluorophores are radioactive labels and enzyme labels. These are likewise known in the art. Flow cytometry methods and instrumentation are known in the art. Descriptions of instrumentation and methods can be found, e.g., in Introduction to Flow Cytometry: A Learning Guide (2000) Becton, Dickinson, and Company; McHugh, "Flow Microsphere Immunoassay for the Quantitative and Simultaneous Detection of Multiple Soluble Analytes," Methods in Cell Biology 42, Part B (Academic Press, 1994).

The disclosed invention also pertains to kits and compositions for the detection of neutralizing antibodies, protective antibodies, high avidity neutralizing antibodies, and/or high avidity protective antibodies specific for SARS-CoV-2 spike protein variants or fragments thereof in a subject. The singleplex and/or multiplex assay disclosed herein provides for the detection and/or quantification of neutralizing antibodies (e.g., immunoglobulin G (IgG) antibodies, IgA, and/or IgM antibodies) specific for SARS-CoV-2 spike protein variants or fragments thereof. The multiplex assay disclosed herein also provides for the detection and/or quantification of high avidity neutralizing antibodies specific for the SARS-CoV-2 spike protein, SARS-CoV-2 spike protein variants or fragments thereof. In certain embodiments, the kits and compositions for the detection of neutralizing antibodies can contain chaotropic agents. The chaotropic agents can be ionic, such as, for example, sodium chloride and sodium thiocyanate, or non-ionic, such as, for example, urea.

Neutralizing antibodies can be antibodies generated within an infected or vaccinated subject, for example, a human. Alternatively, neutralizing and/or protective antibodies can be administered as therapeutic agents and the disclosed assays can detect the presence of such antibodies in samples obtained from a treated subject. For example, human neutralizing monoclonal antibodies B38 and H4 (disclosed in Wu et al., *Science,* 2020, 368(5496):1274-1278, which is hereby incorporated by reference in its entirety) or the 47D11 human monoclonal antibody disclosed in Wang et al. (*Nature Communications,* doi.org/

10.1038/s41467-020-16452-w, published 14 May 2020, "A human monoclonal antibody blocking SARS-CoV-2 infection") which is hereby incorporated by reference in its entirety) are therapeutic antibodies that can be administered to a SARS-CoV2 infected subject and the binding of these neutralizing and/or protective antibodies to a SARS-CoV-2 spike protein variant or fragment thereof can be detected using the disclosed multiplex immunoassays. Alternatively, neutralizing antibodies that can be detected in the disclosed multiplex immunoassays include chimeric, humanized or other forms of recombinant antibodies, such as a CDR-grafted antibody, a nanobody, or an antigen-binding portion of any thereof. Other neutralizing and/or protective antibodies include recombinant antibody formats, such as Fv, single domain antibodies (e.g., VH or VL or VHH), scFv, bi, tri or tetra-valent antibodies, Bis-scFv, diabodies, triabodies, tetrabodies and fragments thereof that neutralize SARS-CoV-2 spike protein variants or fragments thereof. Such antibodies can be generated according to methods well-known in the art. Additionally, as would be clear to those skilled in the art, at least one of the antigen binding portions of a bi-valent antibody, tri-valent antibody, tetra-valent antibody, bis-scFv, diabody, triabody, tetrabody or a fragment thereof that specifically binds to and neutralizes a SARS-CoV-2 spike protein variant or fragment thereof.

In certain embodiments, high avidity neutralizing and/or protective antibodies can be distinguished from low avidity neutralizing and/or protective antibodies using chaotropic agents. The chaotropic agents can be added to the immunoassay reactions to destabilize weaker bonds between antibodies and antigens, leaving only high avidity antigen-antibody complexes. After the chaotropic agents are added, low avidity antigen-antibody complexes are destabilized; therefore, the remaining bonded antigen-antibody complexes demonstrate the existence of a high avidity neutralizing antibodies. In certain embodiments, the designation of high or low avidity is a relative designation and not indicative of a specific binding strength. The avidity designation can be relative to other antibodies in the multiplex assay or to antibodies in separate assays. The designation can be determined by adding one or more chaotropic agents to an assay and determining which antibodies remain bound to an antigen. The chaotropic agents can vary in concentration in order to distinguish relative antibody avidity.

The multiplex assay disclosed herein can detect and/or quantify the amount of specific neutralizing antibodies bound to substrates onto which SARS-CoV-2 spike protein variants or fragments thereof are immobilized and, optionally, detect and/or quantify one or more cytokine selected from IL-1beta, IFN-γ, IFNγ-induced protein 10 (IP-10), monocyte chemoattractant protein 1 (MCP-1), IL-4, IL-10, IL-2R, IL-6, granulocyte colony-stimulating factor (G-CSF), macrophage inflammatory protein-1A, and TNF-α (e.g., any combination of one, two, three, four, five, six, seven, eight, nine, ten, or eleven of these analytes) present in a biological sample. In another embodiment, this application provides a multiplex assay that can detect and/or quantify the amount of specific, neutralizing, high avidity antibodies bound to substrates onto which a SARS-CoV-2 spike protein or fragment thereof and/or a SARS-CoV-2 spike protein variant or fragment thereof are immobilized.

Various of the presently described assays offer detection in at least two dimensions, e.g., the identity of the immobilizing bead (e.g., beads bearing a single SARS-CoV-2 spike protein variant or fragment thereof and the presence and/or amount of antibody and/or high avidity neutralizing antibody bound to a SARS-CoV-2 spike protein or fragment thereof or a SARS-CoV-2 spike protein variant or fragment thereof immobilized on the beads and, optionally, the presence and/or amount of one or more cytokine selected from IL-1beta, IFN-γ, IFNγ-induced protein 10 (IP-10), monocyte chemoattractant protein 1 (MCP-1), IL-4, IL-10, IL-2R, IL-6, granulocyte colony-stimulating factor (G-CSF), macrophage inflammatory protein-1A, and TNF-α (e.g., any combination of one, two, three, four, five, six, seven, eight, nine, ten, or eleven of these analytes). This multidimensional aspect allows for a multiplex format, so that more than one analyte can be detected in a single assay.

Thus, one aspect of the invention provides for combinations of substrate populations. These substrate combinations are made up of two or more (e.g., two, three, four, five, six, seven or more) distinct and unique detectable physical parameters (e.g., dye signatures), each distinct and unique detectable physical parameter being associated with a single substrate population.

In some embodiments, the presence and/or amount of neutralizing antibody, protective antibody, high avidity protective antibody, and/or high avidity neutralizing antibody specific to a SARS-CoV-2 spike protein or fragment thereof and/or a SARS-CoV-2 spike protein variant or fragment thereof and, optionally, the presence and/or amount of one or more cytokine are measured in the same single receptacle or vessel (tube, well, cuvette, etc.) in the presence of beads. As discussed above, each bead population carries a specific detectable physical parameter (e.g., dye signature) and a SARS-CoV-2 spike protein variant or fragment thereof or, in some embodiments, a SARS-CoV-2 spike protein or fragment thereof. Thus, the beads can carry a single SARS-CoV-2 spike protein variant or fragment thereof. Bead populations that carry a specific detectable physical parameter (e.g., dye signature) can also be used to detect the presence of a cytokine.

For detecting cytokines present in a sample, cytokine specific antibodies can be immobilized on a solid support (e.g., microparticles, beads, or surface, such as a chip, microtiter plate, membrane, or glass). In some immobilization protocols, carboxylated beads can be activated and esterified before adding antibodies and/or a SARS-CoV-2 spike protein variant or fragment thereof. Carboxyl activation can be achieved using a water soluble carbodiimide, such as 1-cyclohexyl-3-(2-morpholinoethyl) carbodiimide (CMC). Esterification can be achieved using NHS, NHSS or HOBt. After the carboxyl activation and esterification, the antibodies and SARS-CoV-2 spike protein variant or fragment thereof can added to the activated surface in buffers with pH between 6-10. For example sodium acetate buffer pH 5.1, phosphate buffer pH 7.0 with or without detergent (e.g., CHAPS, ionic and zwitterionic detergents). After coupling/immobilization, the solid support can be blocked in buffers containing protein blocker (such as BSA, mouse IgG, bovine gamma globulin (BGG), animal serum (goat, horse, murine)). The protein blocker(s) can be present in amounts ranging from 0.1-10 weight/volume percent.

A first aspect and second aspect of the invention provides a pair of immunoassays. These immunoassay formats provide for the detection of neutralizing antibodies specific for a SARS-CoV-2 spike protein variant or fragment thereof and, optionally, the presence and/or amounts of one or more cytokine. In these immunoassays, a solid support (for example, fluorescently labeled beads (also referred to as dyed beads) that can be distinguished from one another via a different fluorescent dye/signature) is coated with a SARS-CoV-2 spike protein variant or fragment thereof. Another dyed bead (which is differentially labeled) can be coated with one or more antibody specific for a cytokine where cytokines are being detected. The coated solid support(s) are then combined with a patient sample, e.g., a biological sample from an individual suspected of having been exposed to SARS-CoV-2 virus, along with a sample diluent and incubated to facilitate the binding neutralizing antibodies capable of specifically binding to a SARS-CoV-2 spike protein variant or fragment thereof on the coated solid supports. Labeled ACE2 receptor, including truncated, modified ACE2 receptors or ACE2 fusion proteins (e.g., ACE2R-Fc), can, optionally, be incubated along with the sample. In another optional embodiment, the coated solid support(s) is washed to remove unbound sample and labeled ACE2 receptor is then added to the coated solid support(s). Other embodiments omit that addition of labeled ACE2 receptor to the coated solid substrate(s). After incubation, unbound sample can be washed away and labeled anti-Ig (anti-IgG, IgM, IgA, anti-kappa, or anti-lambda) antibodies can be added to allow for detection of neutralizing antibodies from the sample bound to SARS-CoV-2 spike protein variants or fragments thereof immobilized on the solid support. Where one or more cytokine is being detected or quantified in combination with of antibodies that neutralize SARS-CoV-2 spike protein variants or fragments thereof, labeled antibodies specific to the selected cytokine(s) can be used to detect the presence or quantify the cytokine(s). The reaction can be incubated and washed prior to detection using a Bio-Plex 2200, Bio-Plex 200 or Luminex platforms, such as LX-200, Magpix, Flexmap 360, etc. The identity of each assay is determined by the fluorescence signature of the dyed beads, and the amount of a neutralizing antibody captured by the antigen or cytokine is determined by the fluorescence intensity of the attached labeled anti-Ig. The sample fluorescence intensity is compared to a set of standards or calibrators to generate a qualitative, semi-quantitative or quantitative result. Results for each coated protein may be reported individually, as a group or some type of predefined algorithm or any combination thereof. As discussed above, the biological sample can be obtained from a SARS-CoV2 infected individual, an individual treated with neutralizing antibodies specific for SARS-CoV-2 spike protein variants or fragments or an individual vaccinated with a vaccine comprising SARS-CoV2 spike protein, such as the spike protein variants or fragments thereof that are disclosed herein.

In a second aspect of the invention, ACE2 receptor (preferably human ACE2 receptor and/or including truncated, modified ACE2 receptors, or ACE2 fusion proteins) can be used to identify substrates on which SARS-CoV-2 spike protein variants or fragments thereof are immobilized and to which no neutralizing antibodies are bound. This multiplex assay is illustrated in FIG. 1. In this aspect of the invention, the ACE2 receptor can be labeled or unlabeled. Thus, one embodiment provides a population of beads comprising one or more subpopulations of beads onto which SARS-CoV-2 spike protein variants or fragments thereof are immobilized. This population of beads is mixed (contacted) with mixture of ACE2 receptor and a sample or the population of beads is first contacted with a sample, the population of beads is washed and ACE2 receptor is then added to the washed population of beads. After incubation of the washed population of beads with the ACE2 receptor, the population of beads is washed and then contacted with biotinylated antibodies specific for ACE2 receptor. The population of beads is washed to remove unbound biotinylated antibody and streptavidin-PE is added to the population of beads. The population of beads can be washed and then compared to control samples. A negative signal (the absence of a signal or a reduced signal for a SARS-CoV2 spike protein, a given SARS-CoV-2 spike protein variant or fragment thereof) indicates the existence of the neutralizing antibodies in the sample. The biological sample can be obtained from a SARS-CoV2 infected individual, an individual treated with neutralizing antibodies specific for SARS-CoV-2 spike protein variants or fragments or an individual vaccinated with a vaccine comprising SARS-CoV2 spike protein, such as the spike protein variants or fragments thereof that are disclosed herein.

A second embodiment utilizes labeled ACE2 receptor, including truncated and/or modified ACE2 receptors, or ACE2 fusion proteins, for the detection SARS-CoV-2 spike protein variants or fragments thereof to which no neutralizing antibody is bound. In this embodiment, a population of beads comprising one or more subpopulations of beads onto which SARS-CoV-2 spike protein variants or fragments thereof are immobilized is provided. This population of beads is mixed (contacted) with mixture of labeled ACE2 receptor and a sample or the population of beads is first contacted with a sample, the population of beads is washed and labeled ACE2 receptor is then added to the washed population of beads. The population of beads is washed to remove unbound labeled-ACE2 receptor and serum proteins (e.g., antibodies) and then compared to control samples. A negative signal (the absence of a signal or a reduced signal for a SARS-CoV-2 spike protein, a given SARS-CoV-2 spike protein variant or fragment thereof) indicates the existence of the neutralizing antibodies in the sample. The biological sample can be obtained from a SARS-CoV2 infected individual, an individual treated with neutralizing antibodies specific for SARS-CoV-2 spike protein variants or fragments or an individual vaccinated with a vaccine comprising SARS-CoV2 spike protein, such as the spike protein variants or fragments thereof that are disclosed herein.

A third aspect of the invention provides immunoassays for the detection of high avidity antibodies. In these immunoassays, a solid support (for example, fluorescently labeled beads (also referred to as dyed beads) that can be distinguished from one another via a different fluorescent dye/signature) is coated with a SARS-CoV-2 spike protein or a fragment thereof or a SARS-CoV-2 spike protein variant or fragment thereof. The coated solid support(s) are then combined with a patient sample, e.g., a biological sample from an individual suspected of having been exposed to SARS-CoV-2 virus, along with a sample diluent and incubated to facilitate the binding of neutralizing antibodies capable of specifically binding to a SARS-CoV-2 spike protein or a fragment thereof or a SARS-CoV-2 spike protein variant or fragment thereof on the coated solid supports. The biological sample is then removed from the solid support and, optionally washed to remove unbound proteins and antibodies. One or more chaotropic agent (e.g., 1 M NaCL) is then added to the solid support to displace low avidity antibody. After an incubation period, the chaotropic agent(s) and unbound low avidity antibodies are removed (e.g., by centrifugation and aspiration) from the coated solid supports and the coated solid supports can be washed. The coated solid support(s) is washed and labeled or biotinylated ACE2 receptor is then added to the coated solid support(s) and a signal is detected. The presence of high avidity antibodies is determined by a reduced signal or the lack of signal from the labeled ACE2 receptor (relative to a control). The one or more chaotropic agents can be used at a concentration of about 0.1M to about 8M, when added to the coated solid supports to which antibodies are bound. Non-limiting examples of the chaotropic agents are sodium chloride, urea, guanidine hydrochloride, guanidine thiocyanate and/or sodium thiocyanate. The effective concentrations of urea and/or sodium thiocyanate can be between 0.1M and 8M. The effective concentration of guanidine thiocyanate can be between 0.1M and 6M. The effective concentrations of sodium chloride can be between 0.1M and 5M. Then, labeled streptavidin-PE (Phycoerythrin) can be added to allow for detection.

The relative "high" or "low" avidities can be determined by comparing the signals between two or more antibody subpopulations. The signals of the two or more antibody subpopulations can be measured throughout the assay, i.e. before and after the addition of the chaotropic agent. Alternatively, the signals of the two or more antibody subpopulations can be measured at the conclusion of the assay.

Other embodiments omit the addition of labeled ACE2 receptor to the coated solid substrate(s) and utilize labeled anti-Ig antibodies for the detection of high avidity antibodies. In this embodiment, after incubation with one or more chaotropic agent, low avidity antibodies and chaotropic agent are removed and/or washed away and labeled anti-Ig (anti-IgG, IgM, IgA, anti-kappa, or anti-lambda) antibodies can be added to allow for detection of high avidity binding antibodies from the sample that are bound to a SARS-CoV-2 spike protein or fragments thereof or SARS-CoV-2 spike protein variants or fragments thereof immobilized on the solid support. The presence of a signal indicates the presence of high avidity antibodies within the sample, which can be quantified by comparison to control samples. The one or more chaotropic agents can be used at a concentration of about 0.1M to about 10M, when added to the coated solid supports to which antibodies are bound. Non-limiting examples of the chaotropic agents are sodium chloride, urea, guanidine hydrochloride, guanidine thiocyanate, and/or sodium thiocyanate.

A fourth aspect of the invention provides singleplex immunoassays for the detection neutralizing antibodies. In these immunoassays, a solid support (for example, fluorescently labeled beads (also referred to as dyed beads) is coated with a SARS-CoV-2 spike protein or a fragment thereof or a SARS-CoV-2 spike protein variant or fragment thereof. The coated solid support is then combined with a patient sample, e.g., a biological sample from an individual suspected of having been exposed to SARS-CoV-2 virus, along with a sample diluent and incubated to facilitate the binding of neutralizing antibodies capable of specifically binding to a SARS-CoV-2 spike protein or a fragment thereof or a SARS-CoV-2 spike protein variant or fragment thereof on the coated solid supports. The biological sample is then removed from the solid support and, optionally washed to remove unbound proteins and antibodies. The coated solid support is washed and labeled or biotinylated ACE2 receptor is then added to the coated solid support and a signal is detected. The presence of neutralizing antibodies is determined by a reduced signal or the lack of signal from the labeled ACE2 receptor (relative to a control).

Detection of labeled ACE2 receptor or labeled anti-Ig can be performed using a Bio-Plex 2200, Bio-Plex 200 or Luminex platforms, such as LX-200, Magpix, Flexmap 360, etc. The identity of each assay is determined by the fluorescence signature of the dyed beads, and the amount of high avidity neutralizing antibody captured by the SARS-CoV-2 spike protein or fragment thereof or a SARS-CoV-2 spike protein variant or fragment thereof is determined by the fluorescence intensity of the attached labeled anti-Ig or the labeled ACE2 receptor. The sample fluorescence intensity is compared to a set of standards or calibrators to generate a qualitative, semi-quantitative or quantitative result. Alternatively, the neutralizing concentration of the antibody—the concentration at which 50% of the antigens are neutralized—can be determined using serial dilutions. Results for each coated protein may be reported individually, as a group or some type of predefined algorithm or any combination thereof. As discussed above, the biological sample can be obtained from a SARS-CoV2 infected individual, an individual treated with neutralizing and/or protective antibodies specific for SARS-CoV-2 spike protein variants or fragments or an individual vaccinated with a vaccine comprising SARS-CoV2 spike protein, such as the spike protein variants or fragments thereof that are disclosed herein. As discussed above, each of the disclosed immunoassays can utilizes SARS-CoV-2 spike protein variants or fragments thereof as an analyte. In the context of the invention, a fragment of any particular SARS-CoV-2 spike protein variant can comprise about 5 to about 50, about 10 to about 40, about 15 to about 30, about 20, about 10 or about 5 amino acids, provided that the span of amino acids includes one or more amino acid mutation identified in Table 1. As discussed above, fragments of a SARS-CoV-2 spike protein variant can range in length from 5 amino acids to (n–1) consecutive amino acids of the protein, where n is the total length of the SARS-CoV-2 spike protein, the S1 fragment of the spike protein or the S2 fragment of the spike protein. Thus, for the spike protein, the fragment length is between 5 and 1272 consecutive amino acids in length. In one embodiment, a fragment of the spike protein spans amino acids 13-1213 of the spike protein sequence. In another embodiment, the fragment is the RBD of the S1 protein or a fragment of the RBD. For the S1 protein (amino acids 13-685 of the disclosed spike protein length), a fragment is between 5 and 672 consecutive amino acids of the S1 sequence. For the S2 protein (amino acids 686-1273 of the disclosed spike protein), the fragment length is between 5 and 588 consecutive amino acids in length.

SARS-CoV-2 Spike Protein (1273 AA MW 141178)
SARS-CoV-2 S1 Protein (AA 13-685)
SARS-CoV-2 S2 Protein (AA 686-4273)

SEQ ID NO: 1

MFVFLVLLPLVSSQCVNLTTRTQLPPAYTNSFTRGVYYPDKVFRSSVLHSTQDLFLPFFSNV

TWFHAIHVSGTNGTKRFDNPVLPFNDGVYFASTEKSNIIRGWIFGTTLDSKTQSLLIVNNAT

NVVIKVCEFQFCNDPFLGVYYHKNNKSWMESEFRVYSSANNCTFEYVSQPFLMDLEGKQGNF

KNLREFVFKNIDGYFKIYSKHTPINLVRDLPQGFSALEPLVDLPIGINITRFQTLLALHRSY

LTPGDSSSGWTAGAAAYYVGYLQPRTFLLKYNENGTITDAVDCALDPLSETKCTLKSFTVEK

-continued

GIYQTSNFRVQPTESIVRFPNITNLCPFGEVXMATRFASVYAWXRKRISNCVADYSXLYNSA

SFSTFKCYGVSPTKLNDLCFTNVYADSFVIRGDEVRQIAPGQTGKIADYNYKLPDDFTGCVI

XWNSNNLDSKVGGNYNYLYRLFRXSNLKPFERDISTEIYQAGSTPCNGXEGFNCYFPLQSYG

FQPTNGVGYQPYRVVVLSFELLHAPATVCGPKKSTNLVKNKCVNFNFNGLTGTGVLTESNKK

FLPFQQFGRDIADTTDAVRDPQTLEILDITPCSFGGVSVITPGTNTSNQVAVLYQDVNCTEV

PVAIHADQLTPTWRVYSTGSNVFQTRAGCLIGAEHVNNSYECDIPIGAGICASYQTQTNSPR

XAXSVASQSIIAYTMSLGAENSVAYSNNSIAIPTNFTISVTTEXLPVSMTKTSVDCTMYICG

DSTECSNLLLQYGSFCTQLNRALTGIAVEQDKNTQEVFAQVKQIYKTPPIKDFGGFNFSQIL

PDPSKPSKRSFIEDLLFNKVTLADAGFIKQYGDCLGDIAARDLICAQKFNGLTVLPPLLTDE

MIAQYTSALLAGTITSGWTFGAGAALQIPFAMQMAYRFNGIGVTQNVLYENQKLIANQFNSA

IGKIQDSLSSTASALGKLQDVVNQNAQALNTLVKQLSSNFGAISSVLNDILSRLDXXEAEVQ

IDRLITGRLQSLQTYVTQQLIRAAEIRASANLAATKMSECVLGQSKRVDFCGKGYHLMSFPQ

SAPHGVVFLHVTYVPAQEKNFTTAPAICHDGKAHFPREGVFVSNGTHWFVTQRNFYEPQIIT

TDNTFVSGNCDVVIGIVNNTVYDPLQPELDSFKEELDKYFKNHTSPDVDLGDISGINASVVN

IQKEIDRLNEVAKNLNESLIDLQELGKYEQYIKWPWYIWLGFIAGLIAIVMVTIMLCCMTSC

CSCLKGCCSCGSCCKFDEDDSEPVLKGVKLHYT

>QJF75467.1 surface glycoprotein [Severe acute respiratory syndrome coronavirus 2]
SARS-CoV-2 Spike Protein (1273 AA MW 141178)
SARS-CoV-2 S1 Protein (AA 13-685)
SARS-CoV-2 S2 Protein (AA 6861273)

SEQ ID NO: 2

MFVFLVLLPLVSSQCVNLTTRTQLPPAYTNSFTRGVYYPDKVFRSSVLHSTQDLFLPFFSNV

TWFHAIHVSGTNGTKRFDNPVLPFNDGVYFASTEKSNIIRGWIFGTTLDSKTQSLLIVNNAT

NVVIKVCEFQFCNDPFLGVYYHKNNKSWMESEFRVYSSANNCTFEYVSQPFLMDLEGKQGNF

KNLRSFVFKNIDGYFKIYSKHTPINLVRQLPQGFSALEPLVDLPIGINITRFQTLLALHRSY

LTPGDSSSGWTAGAAAYYVGYLQPRTFLLKYNENGTITDAVDCALDPLSETKCTLKSFTVEK

GIYQTSNFRVQPTESIVRFPNITNLCPFGEVXNATRFASVYAWXRKRISNCVADYSXLYNSA

SFSTFKCYGVSPTKLNDLCFTNVYADSFVIRGDEVRQIAPGQTGKIADYNYKLFDDFTGCVI

XWNSNNLDSKVGGNYNYLYRLFRXSNLKPFERDISTEIYQAGSTPCNGXEGFNCYFPLQSYG

FQPTNGVGYQPYRVVVLSFELLHAPATVCGPKKSTNLVKNKCVNFNFNGLTGTGVLTESNKK

FLPFQQFGRDIADTTDAVRDPQTLEILDITPCSFGGVSVITPGTNTSNQVAVLYQDVNCTEV

PVAIHADQLTPTWRVYSTGSNVFQTRAGCLIGAEHVNNSYECDIPIGAGICASYQTQTNSPR

XAXSVASQSIIAYTMSLGAENSVAYSNNSIAIPTNFTISVTTEILPVSMTKTSVDCTMYICG

DSTECSNLLLQYGSFCTQLNRALTGIAVEQDKNTQEVFAQVKQIYKTPPIKDFGGFNFSQIL

PDPSKPSKRSFIEDLLFNKVTLADAGFIKQYGDCLGDIAARDLICAQKFNGLTVLPPLLTDE

MIAQYTSALLAGTITSGWTFGAGAALQIPFAMQMAYRFNGIGVTQNVLYENQKLIANQFNSA

IGKIQDSLSSTASALGKLQDVVNQNAQALNTLVKQLSSNFGAISSVLNDILSRLDXXEAEVQ

IDRLITGRLQSLQTYVTQQLIRAAEIRASANLAATKMSECVLGQSKRVDFCGKGYHLMSFPQ

SAPHGVVFLHVTYVPAQEKNFTTAPAICHDGKAHFPREGVFVSNGTHWFVTQRNFYEPQIIT

TDNTFVSGNCDVVIGIVNNTVYDPLQPELDSFKEELDKYFKNHTSPDVDLGDISGINASVVN

IQKEIDRLNEVAKNLNESLIDLQELGKYEQYIKWPWYIWLGFIAGLIAIVMVTIMLCCMTSC

CSCLKGCCSCGSCCKFDEDDSEPVLKGVKLHYT

YP_909724390.1 surface glycoprotein [Severe acute respiratory syndrome coronavirus 2]
SARS-CoV-2 Spike Protein (1273 AA MW 141178)

-continued

SARS-CoV-2 S1 Protein (AA 13-685)
SARS-CoV-2 S2 Protein (AA 686-1273)

SEQ ID NO: 3

MFVFLVLLPLVSSQCVNLTTRTQLPPAYTNSFTRGVYYPDKVFRSSVLHSTQDLFLPFFSNV

TWFHAIHVSGTNGTKRFDNPVLPFMDGVYFASTEKSMIIRGWIFGTTLDSKTQSLLIVNNAT

NVVIKVCEFQFCNDPFLGVYYHKNNKSWMESEFRVYSSANNCTFEYVSQPFLMDLEGKQGNF

KNLREFVFKNIDGYFKIYSKHTPINLVRDLPQGFSALEPLVDLPIGINITRFQTLLALHRSY

LTPGDSSSGWTAGAAAYYVGYLQPRTFLLKYNENGTITDAVDCALDPLSETKCTLKSFTVEK

GIYQTSNFRVQPTESIVRFPNITNLCPFGEVFNATRFASVYAWNRKRISNCVADYSVLYNSA

SFSTFKCYGVSPTKLNDLCFTNVYADSFVIRGDEVRQIAPGQTGKIADYNYKLPDDFTGCVI

AWNSNNLDSKVGGNYNYLYRLFRKSNLKPFERDISTEIYQAGSTPCNGVEGFNCYFPLQSYG

FQPTNGVGYQPYRVVVLSFELLHAPATVCGPKKSTNLVKNKCVNFNFNGLTGTGVLTESNKK

FLPFQQFGRDIADTTDAVRDPQTLEILDITPCSFGGVSVITPGTNTSNQVAVLYQDVNCTEV

PVAIHADQLTPTWRVYSTGSNVFQTRAGCLIGAEHVNNSYECDIPIGAGICASYQTQTNSPR

RAR/SVASQSIIAYTMSLGAENSVAYSNNSIAIPTNFTISVTTEILPVSMTKTSVDGTMYIC

GDSTSCSNLLLQYGSFCTQLNRALTGIAVEQDKNTQEVFAQVKQIYKTPPIKDFGGFNFSQI

LPDPSKPSKRSFIEDLLFNKVTLADAGFIKQYGDCLGDIAARDLICAQKFNGLTVLPPLLTD

EMIAQYTSALLAGTITSGWTFGAGAALQIPFAMQMAYRFNGIGVTQNVLYENQKLIANQFNS

AIGKIQDSLSSTASALGKLQDVVNQNAQALNTLVKQLSSNFGAISSVLNDILSRLDKVEAEV

QIDRLITGRLQSLQTYVTQQLIRAAEIRASANLAATKMSECVLGQSKRVDFCGKGYHLMSFP

QSAPHGVVFLHVTYVPAQEKNFTTAPAICHDGKAHFPREGVFVSNGTHWFVTQRNFYEPQII

TTDNTFVSGNCDVVIGIVNNTVYDPLQPELDSFKEELDKYFKNHTSPDVDLGDISGINASVV

NIQKEIDRLNEVAKNLNESLIDLQELGKYEQYIKWPWYIWLGFIAGLIAIVMVTIMLCCMTS

CCSCLKGCCSCGSCCKFDEDDSEPVLKGVKLHYT

ACE2 [Homo sapiens]
GenBank: BAB40370.1
>BAB40370.1 ACE2 [Homo sapiens]

SEQ ID NO: 4

MSSSSWLLLSLVAVTAAQSTIEEQAKTFLDKFNHEAEDLFYQSSLASWNYNTNITEENVQNM

NNAGDKWSAFLKEQSTLAQMYPLQEIQNLTVKLQLQALQQNGSSVLSEDKSKRLNTILNTMS

TIYSTGKVCNPDNPQECLLLEPGLNEIMANSIDYNERLWAWESWRSEVGKQLRPLYEEYVVL

KNEMARANHYEDYGDYWRGDYEVNGVDGYDYSRGQLIEDVEHTFEEIKPLYEHLHAYVRAKL

MNAYPSYISPIGCLPAHLLGDMWGRFWTNLYSLTVPFGQKPNIDVTDAMVDQAWDAQRIFKE

AEKFFVSVGLPNMTQGFWENSMLTDPGNVQKAVCHPTAWDLGKGDFRILMCTKVTMDDFLTA

HHEMGHIQYDMAYAAQPFLLRNGANEGFHEAVGEIMSLSAATPKHLKSIGLLSPDFQEDNET

EINFLLKQALTIVGTLPFTYMLEKWRWMVFKGEIPKDQWMKKWWEMKREIVGVVEPVPHDET

YCDPASLFHVSNDYSFIRYYTRTLYQFQFQEALCQAAKHEGPLHKCDISNSTEAGQKLFNML

RLGKSEPWTIALENVVGAKNMNVRPLLNYFEPLFTWLKDQNKNSFVGWSTDWSPYADQSIKV

RISLKSALGDRAYEWMDNEMYLFRSSVAYAMRQYFLKVKNQMILFGEEDVRVANLKPRISFN

FFVTAPKNVSDIIPRTEVEKAIRMSRSRINDAFRLNDNSLEFLGIQPTLGPPNQPPVSIWLI

VFGVVMGVIVVGIVILIFTGIRDRKKKNKARSGENPYASIDISKGENNPGFQNTDDVQTSF

Various non-limiting embodiments include:

1. A substrate comprising a population of particles or beads comprising two or more separate subpopulations of particles or beads, each subpopulation of particles or beads being distinguishable by a specific detectable parameter and each subpopulation of beads comprising a distinct SARS-CoV-2 spike protein variant or fragment thereof immobilized thereon and, optionally, a further subpopulation of beads comprising a SARS-CoV-2 spike protein or fragment thereof immobilized thereon.

2. The substrate according to embodiment 1, wherein said substrate is glass, plastic, polystyrene or nitrocellulose.

3. The substrate according to embodiment 1 or 2, wherein said substrate is a particle.

4. The substrate according to embodiment 1 or 2, wherein said substrate is a bead.

5. The substrate according to embodiment 4, wherein said population comprises two or more separate subpopulations of particles or beads selected from:

a) a SARS-CoV-2 spike protein variant or fragment thereof containing the mutation V367X immobilized on a first particle or bead having a first specific detectable physical parameter, where X is any amino acid or X is F;

b) a SARS-CoV-2 spike protein variant or fragment thereof containing the mutation F342X immobilized on a second particle or bead having a second specific detectable physical parameter, where X is any amino acid or X is L;

c) a SARS-CoV-2 spike protein variant or fragment thereof containing the mutation A435X immobilized on a third particle or bead having a third specific detectable physical parameter, where X is any amino acid or X is S;

d) a SARS-CoV-2 spike protein variant or fragment thereof containing the mutation K458X immobilized on a fourth particle or bead having a fourth specific detectable physical parameter, where X is any amino acid or X is R;

e) a SARS-CoV-2 spike protein variant or fragment thereof containing the mutation V483X immobilized on a fifth particle or bead having a fifth specific detectable physical parameter, where X is any amino acid or X is A;

f) a SARS-CoV-2 spike protein variant or fragment thereof containing the mutation V483X immobilized on a sixth particle or bead having a sixth specific detectable physical parameter, where X is any amino acid or X is A;

g) a SARS-CoV-2 spike protein variant or fragment thereof containing the mutation N354X immobilized on a seventh particle or bead having a seventh specific detectable physical parameter, where X is any amino acid or X is D;

h) a SARS-CoV-2 spike protein variant or fragment thereof containing the mutations R683X1 and/or R685X2 immobilized on an eighth particle or bead having an eighth specific detectable physical parameter, where X1 and X2 are any amino acid or X1 and X2 are A;

i) a SARS-CoV-2 spike protein variant or fragment thereof containing the mutations K986X3 and/or V987X4 immobilized on a ninth particle or bead having a ninth specific detectable physical parameter, where X3 and X4 are any amino acid or X3 and X4 are P;

j) a SARS-CoV-2 spike protein variant or fragment thereof containing the mutations R683X1, R685X2, K986X3, and V987X4 immobilized on a tenth particle or bead having a tenth specific detectable physical parameter, where X1 is any amino acid or X1 is A; X2 is any amino acid or X2 is A; X3 is any amino acid or X3 is P; and X4 is any amino acid or X4 is P; and k) a SARS-CoV-2 spike protein or fragment thereof immobilized on an eleventh particle or bead having an eleventh specific detectable physical parameter.

6. The substrate according to embodiment 5, wherein said population of particles or beads comprises two, three, four, five, six, seven, eight, nine, ten or more subpopulations of particles or beads, each subpopulation having a specific detectable physical parameter.

7. The substrate according to any one of embodiments 4-6, wherein the specific detectable physical parameter is a fluorescent dye (fluorophore), luminescent agent, electron-dense reagent, radioisotope or particle size.

8. The substrate according to embodiment 7, wherein the specific detectable parameter is a fluorophore.

9. A method for detecting neutralizing and/or protective antibodies in a mammal comprising obtaining a biological sample from the mammal, contacting said biological sample with a substrate comprising a substrate according to any one of embodiments 1-8 and detecting the presence or absence of neutralizing antibodies bound to SARS-CoV-2 spike protein variants or fragments thereof on the surface of said substrate.

10. The method according to embodiment 9, wherein the mammal is a human, non-human primate, canine, or feline.

11. The method according to any one of embodiments 9-10, wherein the presence or absence of neutralizing antibodies comprises contacting the substrate with human ACE2 receptor and detecting the presence or absence of ACE2 receptor binding to substrate subpopulations onto which SARS-CoV-2 spike protein variants or fragments thereof have been immobilized, the detection of ACE2 receptor binding to a substrate subpopulation indicated a lack of neutralizing antibody specific for a specific a SARS-CoV-2 spike protein variant or fragment thereof.

12. The method according to embodiment 11, wherein ACE2 receptor binding to a substrate subpopulation is detected using an antibody specific for ACE2 receptor that is detectably labeled.

13. The method according to embodiment 11, wherein ACE2 receptor binding to a substrate subpopulation is detected using ACE2 receptor that is detectably labeled.

14. The method according to embodiment 13, wherein the ACE2 receptor is labeled with phycoerythrin (PE) or is biotinylated and detected using streptavidin-PE.

15. The method according to embodiment 9 or 10, wherein neutralizing antibody bound to a substrate comprising a given a SARS-CoV-2 spike protein variant or fragment thereof is detected using a species specific anti-immunoglobulin (Ig) antibody.

16. The method according to embodiment 15, wherein the anti-Ig antibody is biotinylated and binding to neutralizing antibody is detected with a labeled avidin or streptavidin.

17. The method according to embodiment 15, wherein the anti-Ig antibody is labeled.

18. The method according to embodiment 16 or embodiment 17, wherein the label is a fluorophore.

19. The method according to embodiment 18, wherein the fluorophore is PE.

20. The method according to any one of embodiments 9-19, said method further comprising detecting the presence, absence or amounts of cytokines selected from IL-1beta, IFN-γ, IFNγ-induced protein 10 (IP-10), monocyte chemoattractant protein 1 (MCP-1), IL-4, IL-10, IL-2R, IL-6, granulocyte colony-stimulating factor (G-CSF), macrophage inflammatory protein-1A, and TNF-α in said biological sample.

21. The method according to embodiment 20, wherein the detection of said one or more cytokine comprises contacting one or more subpopulations of beads onto which cytokines are immobilized by an antibody specific for each selected cytokine and detecting bound cytokine with antibodies specific for the cytokine and determining the fluorescence intensity for each subpopulation of beads to which cytokines are bound.

22. The method according to embodiment 21, the sample fluorescence intensity is compared to a set of standards or calibrators to generate a qualitative, semi-quantitative or quantitative result.

23. The method according to any one of embodiments 20-22, wherein said detection comprises contacting the substrate contacted with said biological sample with anti-immunoglobulin (anti-Ig) antibodies and, optionally, cytokine specific antibodies that are detectably labeled with a fluorescent dye (fluorophore), luminescent agent, electron-dense reagent, or radioisotope.

24. The method according to embodiment 23, wherein said anti-Ig antibodies are detectably labeled with a fluorophore and said anti-cytokine antibodies are labeled with a fluorophore, and when assayed, and the sample fluorescence intensity is compared to a set of standards or calibrators to generate a qualitative, semi-quantitative or quantitative result.

25. The method according to any one of embodiments 20-22, wherein said detection comprises contacting the substrate contacted with said biological sample with anti-Ig antibodies and cytokine specific antibodies, when assayed, that are biotinylated and contacting said biotinylated antibodies with a biotin-binding ligand that is detectably labeled and determining the fluorescence intensity for each subpopulation of beads.

26. The method according to embodiment 25, the sample fluorescence intensity is compared to a set of standards or calibrators to generate a qualitative, semi-quantitative or quantitative result of total Ig bound to said substrate.

27. The method according to any one of embodiments 20-26, wherein said one or more cytokine is IL-6 and/or IL-2R.

28. The method according to any one of embodiments 20-27, wherein said one or more cytokine is selected from IL-6, IL-2R, granulocyte colony-stimulating factor, IP-10, MCP-1, macrophage inflammatory protein-1A, TNF-α, and combinations thereof.

29. The method according to any one of embodiments 9-28, wherein the neutralizing antibody is a polyclonal antibody or a monoclonal antibody.

30. The method according to embodiment 29, wherein the polyclonal or monoclonal antibody is a human polyclonal or a human monoclonal antibody.

31. The method according to embodiment 29, wherein the neutralizing antibody is a recombinant antibody selected from a humanized antibody, a chimeric antibody, a CDR-grafted antibody, a nanobody, a Fv, a single domain antibody, such as a VH, a VL or VHH, a scFv, a bi-valent antibody, a tri-valent antibody, a tetra-valent antibodies, bis-scFv, diabodies, triabodies, tetrabodies and fragments thereof, provided that at least one of the antigen binding portions of said bi-valent antibody, tri-valent antibody, tetra-valent antibody, bis-scFv, diabodies, triabodies, tetrabodies or fragments thereof neutralizes a SARS-CoV-2 spike protein variant or fragment thereof.

32. A method for detecting high avidity neutralizing antibodies in a mammal comprising obtaining a biological sample from the mammal, contacting said biological sample with a substrate comprising a substrate according to any one of embodiments 1-8 and detecting the presence or absence of high avidity neutralizing antibodies bound to SARS-CoV-2 spike protein variants or fragments thereof on the surface of said substrate.

33. The method according to embodiment 32, wherein the mammal is a human, non-human primate, canine, or feline.

34. The method according to any one of embodiment 32-33, wherein the method comprises:
a) contacting the substrate with the biological sample;
b) optionally removing the biological sample from the substrate and washing the substrate to remove unbound material and antibody;
c) contacting the substrate with one or more chaotropic agents;
d) removing the one or more chaotropic agents from the substrate;
e) optionally, washing the substrate; and
f) detecting the presence or absence of high avidity neutralizing antibody binding to substrate subpopulations onto which SARS-CoV-2 spike protein or fragments thereof and SARS-CoV-2 spike protein variants or fragments thereof have been immobilized.

35. The method according to embodiment 34, wherein the chaotropic agent is sodium chloride, sodium thiocyanate, and/or urea.

36. The method according to embodiments 32-35, wherein the method comprises detecting SARS-CoV-2 spike protein or fragments thereof and/or SARS-CoV-2 spike protein variants or fragments thereof present on the substrate with an ACE2 receptor.

37. The method according to embodiment 36, wherein ACE2 receptor binding to the substrate is detected using ACE2 receptor that is detectably labeled or with an antibody specific for the ACE2 receptor that is detectably labeled.

38. The method according to embodiment 37, wherein the ACE2 receptor is labeled with phycoerythrin (PE) or is biotinylated and detected using streptavidin-PE.

39. The method according to any one of embodiments 32-35, wherein high avidity neutralizing antibody bound to a substrate comprising a given a SARS-CoV-2 spike protein or fragment thereof and/or a SARS-CoV-2 spike protein variant or fragment thereof is detected using a species specific anti-immunoglobulin (Ig) antibody.

40. The method according to embodiment 39, wherein the anti-Ig antibody is biotinylated and binding to neutralizing antibody is detected with a labeled avidin or streptavidin.

41. The method according to embodiment 39, wherein the anti-Ig antibody is labeled.

42. The method according to embodiment 40 or embodiment 41, wherein the label is a fluorophore.

43. The method according to embodiment 42, wherein the fluorophore is PE.

44. A method for detecting a neutralizing antibody in a mammal comprising obtaining a biological sample from the mammal, contacting said biological sample with a substrate according to embodiment 1 and detecting the presence or absence of a neutralizing antibody bound to a SARS-CoV-2 spike protein variant or fragment thereof on the surface of said substrate, said biological sample being obtained from individuals suspected of infection by the virus, treated with SARS-CoV-2 neutralizing antibodies or convalescent plasma, or immunized with a vaccine comprising the SARS-CoV2 spike protein.

45. The method according to embodiment 44, wherein the mammal is a human, non-human primate, canine, or feline.

46. The method according to any one of embodiment 44-45, wherein the method comprises:
a) contacting the substrate with the biological sample;
b) optionally removing the biological sample from the substrate and washing the substrate to remove unbound material and antibody; and
c) detecting the presence or absence of a neutralizing antibody binding to a substrate population onto which a SARS-CoV-2 spike protein or fragment thereof or SARS-CoV-2 spike protein variant or fragment thereof has been immobilized.

47. The method according to embodiments 44-46, wherein the method comprises detecting a SARS-CoV-2 spike protein or fragment thereof or SARS-CoV-2 spike protein variant or fragment thereof present on the substrate with an ACE2 receptor.

48. The method according to embodiment 47, wherein ACE2 receptor binding to the substrate is detected using ACE2 receptor that is detectably labeled or with an antibody specific for the ACE2 receptor that is detectably labeled.

49. The method according to embodiment 48, wherein the ACE2 receptor is labeled with phycoerythrin (PE) or is biotinylated and detected using streptavidin-PE.

50. The method according to embodiment 49, wherein the ACE2 receptor is a biotinylated ACE2-Fc fusion and is detected using streptavidin-PE.

51. The method according to any preceding embodiment, wherein the ACE2 receptor is a truncated or modified ACE2 receptor or is an ACE2 receptor fusion protein.

52. The method according to embodiment 51, wherein the ACE2 receptor fusion protein comprises an immunoglobulin Fc domain fused to the carboxyl-terminus of the ACE2 receptor.

53. The method according to embodiment 52, wherein the fusion protein is biotinylated on the Fc domain.

EXAMPLES

Example 1—Measurement of Neutralizing Antibodies Specific for SARS-CoV-2 Spike Protein Variants or Fragments Thereof A population of fluorescently labeled beads comprising a plurality of subpopulations of fluorescently labeled beads to which individual SARS-CoV-2 spike protein variants or fragments thereof are immobilized is contacted with a patient sample, e.g., a biological sample from an individual suspected of having been exposed to SARS-CoV-2 or a subject immunized with a vaccine comprising SARS-CoV2 spike protein along with a sample diluent. After incubation unbound sample was washed away and biotinylated human ACE2 receptor is added to the washed beads and incubated. Unbound biotinylated human ACE2 receptor is then washed away and labeled streptavidin-PE (Phycoerythrin) is added. The reaction is incubated and then washed prior to detection using a Bio-Plex 2200, Bio-Plex 200 or Luminex LX-200 platform. The sample fluorescence intensity is compared to the fluorescence intensity of a set of standards or calibrators to generate a qualitative, semi-quantitative or quantitative result. A lack of signal for a particular subpopulation of beads onto which a SARS-CoV-2 spike protein variant or fragment thereof has been immobilized indicates neutralizing antibody to that SARS-CoV-2 spike protein variant or fragment thereof are present in the sample. The presence of a signal for a particular subpopulation of beads onto which a SARS-CoV-2 spike protein variant or fragment thereof has been immobilized indicates that there are no neutralizing antibodies in the sample.

Figure 4:
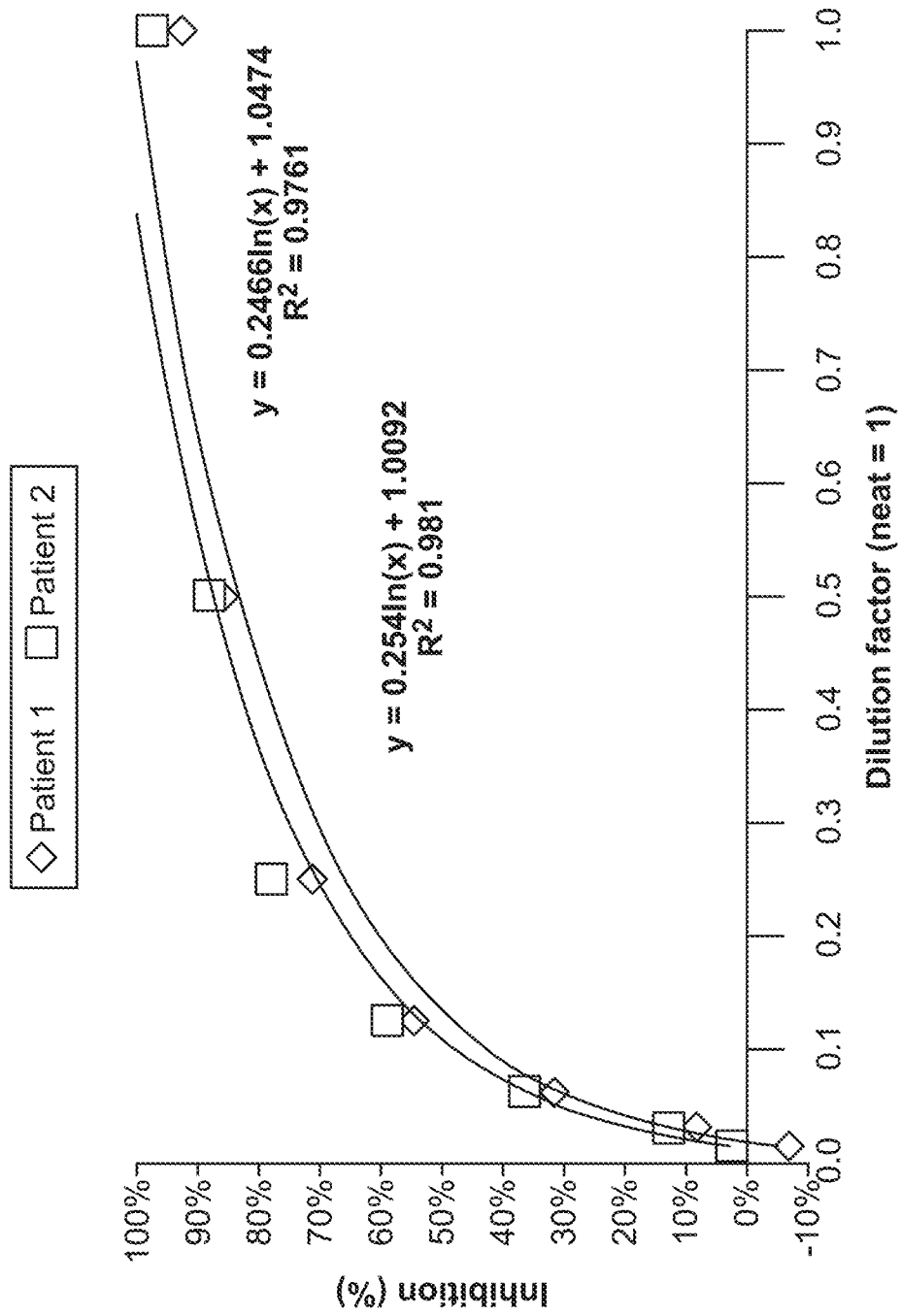
FIG. 4 illustrates a neutralizing antibody inhibition curve of the RBD-biotinylated ACE2 interaction with sera from two COVID 19 patients. % inhibition=1−(relative fluorescent intensity (RFI) of each diluted samples/Matrix RFI).

FIG. 4 shows percent inhibition of the RBD-biotinylated ACE2 interaction by sera from two COVID-19 patients. Samples were diluted serially in the base matrix and tested for the presence of neutralizing antibodies by the Bio-Plex 2200 assay. The neutralization potency was quantified by calculating the half maximal inhibitory concentration ($IC_{50}$) of each sample. The percent inhibition is calculated using the following formula: 1−(RFI of each diluted samples/Matrix RFI). Sample 1 showed an $IC_{50}$ at a 0.135 dilution, sample 2 demonstrated an $IC_{50}$ at 0.110 dilution of the original sample. These results support the utility of the Bio-Plex 2200 assay in quantitating neutralizing antibodies.

Example 2—Multiplex Detection of Neutralizing Antibodies Specific for SARS-CoV-2 Spike Protein Variants or Fragments Thereof A population of fluorescently labeled beads comprising a plurality of subpopulations of fluorescently labeled beads to which individual SARS-CoV-2 spike protein variants or fragments thereof are immobilized is contacted with a patient sample, e.g., a biological sample from an individual suspected of having been exposed to SARS-CoV-2 or a subject immunized with a vaccine comprising SARS-CoV2 spike protein along with a sample diluent. After incubation unbound sample was washed away and human ACE2 receptor is added to the washed beads and incubated. Unbound human ACE2 receptor is then washed away. Biotinylated antibody specific for human ACE2 receptor is added. The reaction is incubated and then washed and streptavidin-PE is added to the washed population of beads and incubated. After incubation, the population of beads is washed prior to detection using a Bio-Plex 2200, Bio-Plex 200 or Luminex LX-200 platform. The sample fluorescence intensity is compared to the fluorescence intensity of a set of standards or calibrators to generate a qualitative, semi-quantitative or quantitative result. A lack of signal for a particular subpopulation of beads onto which a SARS-CoV-2 spike protein variant or fragment thereof has been immobilized indicates neutralizing antibody to that SARS-CoV-2 spike protein variant or fragment thereof are present in the sample. The presence of a signal for a particular subpopulation of beads onto which a SARS-CoV-2 spike protein variant or fragment thereof has been immobilized indicates that there are no neutralizing antibodies in the sample.

Example 3—Multiplex Detection of Neutralizing Antibody for SARS-CoV-2 Spike Protein Variants or Fragments Thereof and IL-6

A population of fluorescently labeled beads comprising: 1) a subpopulation of fluorescently labeled beads to which antibodies specific to IL-6 have been immobilized; and 2) one or more subpopulations of fluorescently labeled beads to which SARS-CoV-2 spike protein variants or fragments thereof have been immobilized is combined with patient sample, e.g., a biological sample from an individual suspected of having been exposed to SARS-CoV-2 virus or a biological sample from a subject vaccinated with a vaccine comprising spike protein. After incubation unbound sample is washed away. Biotinylated antibody specific for IL-6 and biotinylated human ACE2 receptor is added to the washed beads and allowed to incubate. The biotinylated antibody binds to IL-6 bound to the beads on which antibodies specific to IL-6 have been immobilized and biotinylated human ACE2 receptor binds to SARS-CoV-2 spike protein variant or fragment thereof immobilized on a relevant subpopulation of beads to which no neutralizing antibody is bound. Unbound biotinylated reagents are then washed away and labeled streptavidin-PE (phycoerythrin) is added to allow for detection of IL-6 in the sample and beads to which no neutralizing antibody was bound to a given SARS-CoV-2 spike protein variant or fragment thereof. The reaction is incubated and then washed prior to detection using a Bio-Plex 2200, Bio-Plex 200 or Luminex LX-200 platform. The identity of bead subpopulation is determined by the fluorescence signature of the dyed beads, and the amount and/or presence of IL-6 is determined by the fluorescence intensity of the bound labeled Streptavidin. The sample fluorescence intensity is compared to the fluorescence intensity of a set of standards or calibrators to generate a qualitative, semi-quantitative or quantitative result. A lack of signal for a particular subpopulation of beads onto which a SARS-CoV-2 spike protein variant or fragment thereof has been immobilized indicates neutralizing antibody to that SARS-CoV-2 spike protein variant or fragment thereof are present in the sample. The presence of a signal for a particular subpopulation of beads onto which a SARS-CoV-2 spike protein variant or fragment thereof has been immobilized indicates that there are no neutralizing antibodies in the sample.

Example 4—Multiplex Detection of Neutralizing Antibodies Specific for SARS-CoV-2 Spike Protein Variants or Fragments Thereof and IL-6

A population of fluorescently labeled beads comprising: 1) one or more subpopulations of fluorescently labeled beads to which SARS-CoV-2 spike protein variants or fragments thereof have been immobilized; and 2) a subpopulation of fluorescently labeled beads to which monoclonal and/or polyclonal antibodies specific for IL-6 have been immobilized is combined with patient sample, e.g., a biological sample from an individual suspected of having been exposed to SARS-CoV-2 virus or immunized with a SARS-CoV-2 vaccine comprising spike protein. After incubation unbound sample is washed away. Human ACE2 receptor is added to the washed beads and allowed to incubate. Unbound human ACE2 receptor is washed away and biotinylated antibody specific for human ACE 2 and biotinylated antibody specific for IL-6 is added to the washed beads and allowed to incubate. The biotinylated antibody binds to IL-6 bound to antibodies immobilized on its respective bead subpopulation and human ACE2 bound to one or more subpopulations of beads onto which a given spike protein variant or fragment thereof that has been immobilized and to which no neutralizing antibody may then be detected by the addition of streptavidin-labeled PE. Unbound biotinylated reagents are then washed away and labeled streptavidin-PE (Phycoerythrin) is added to allow for detection of IL-6 and bound neutralizing antibody specific for a spike protein variant or fragment thereof. The reaction is incubated and then washed prior to detection using a Bio-Plex 2200, Bio-Plex 200 or Luminex LX-200 platform. The identity of bead subpopulation is determined by the fluorescence signature of the dyed beads, and the amount of IL-6 captured is determined by the fluorescence intensity of the bound labeled streptavidin. The sample fluorescence intensity is compared to the fluorescence intensity of a set of standards or calibrators to generate a qualitative, semi-quantitative or quantitative result. A lack of signal for a particular subpopulation of beads onto which a SARS-CoV-2 spike protein variant or fragment thereof has been immobilized indicates neutralizing antibody to that SARS-CoV-2 spike protein variant or fragment thereof are present in the sample. The presence of a signal for a particular subpopulation of beads onto which a SARS-CoV-2 spike protein variant or fragment thereof has been immobilized indicates that there are no neutralizing antibodies in the sample.

Example 5—Multiplex Detection of Neutralizing Antibodies Specific for SARS-CoV-2 Spike Protein Variants or Fragments Thereof A population of fluorescently labeled beads comprising a plurality of subpopulations of fluorescently labeled beads to which individual SARS-CoV-2 spike protein variants or fragments thereof are immobilized is contacted with a patient sample, e.g., a biological sample from an individual suspected of having been exposed to SARS-CoV-2 or a subject immunized with a vaccine comprising SARS-CoV2 spike protein along with a sample diluent. After incubation unbound sample was washed away and biotinylated antibody specific for human immunoglobulin (anti-IgA, anti-IgM, anti-IgG, anti-kappa chain, and/or anti-lambda chain antibody) is added to the washed beads and incubated. Unbound biotinylated anti-human antibody is then washed away and labeled streptavidin-PE (Phycoerythrin) is added. The reaction is incubated and then washed prior to detection using a Bio-Plex 2200, Bio-Plex 200 or Luminex LX-200 platform. The sample fluorescence intensity is compared to the fluorescence intensity of a set of standards or calibrators to generate a qualitative, semi-quantitative or quantitative result. A lack of signal for a particular subpopulation of beads onto which a SARS-CoV-2 spike protein variant or fragment thereof has been immobilized indicates that no neutralizing antibody to that SARS-CoV-2 spike protein variant or fragment thereof are present in the sample. The presence of a signal for a particular subpopulation of beads onto which a SARS-CoV-2 spike protein variant or fragment thereof has been immobilized indicates that there are neutralizing antibodies in the sample and the amount of neutralizing antibody can also be quantified. The sample fluorescence intensity can be compared to the fluorescence intensity of a set of standards or calibrators to generate a qualitative, semi-quantitative or quantitative result for the amount of neutralizing antibody present in the sample.

Example 6—Multiplex Detection of High Avidity Neutralizing Antibodies Specific for SARS-CoV-2 Spike Protein Variants or Fragments Thereof A population of fluorescently labeled beads comprising a plurality of subpopulations of fluorescently labeled beads to which individual SARS-CoV-2 spike protein variants or fragments thereof are immobilized is contacted with a patient sample, e.g., a biological sample from an individual suspected of having been exposed to SARS-CoV-2 or a subject immunized with a vaccine. A SARS-CoV-2 neutralization assay combines an aliquot of patient sample, chaotropic agent sample diluent at various concentrations, and a biotinylated-human ACE2 protein. Following a short incubation, a bead mixture comprising coupled SARS-CoV-2 spike protein variants, RBD, and mutant variants or fragments thereof are added to the reaction vessel. After a period of incubation at about 37° C., the mixture is washed and the beads are suspended in streptavidin-PE conjugate reagent; the mixture is again incubated at 37° C. The excess unbound conjugate is removed in another wash cycle and the washed beads are resuspended in a wash buffer. The identity of the dyed beads is determined by the fluorescence of the dyes and the amount of biotinylated-human ACE2 captured by the SARS-CoV-2 spike protein variants, RBD and mutant variants or fragments thereof. The fluorescence of the attached phycoerythrin is determined using the Bio-Plex 2200, Bio-Plex 200 or Luminex LX-200 platform to detect binding of biotinylated ACE2 receptor. The sample fluorescence intensity is compared to the fluorescence intensity of a set of standards or calibrators to generate the relative fluorescence intensity (RFI) and, subsequently, a qualitative, semi-quantitative or quantitative result. A lack of signal or a reduced signal for a particular subpopulation of beads onto which a SARS-CoV-2 spike protein (or fragment thereof) or a SARS-CoV-2 spike protein variant or fragment thereof has been immobilized indicates the presence of high avidity neutralizing antibodies and the amount of high avidity antibodies can also be quantitated. The presence of a signal for a particular subpopulation of beads onto which a SARS-CoV-2 spike protein variant or fragment thereof has been immobilized indicates that there are no neutralizing antibodies or there are low avidity neutralizing antibodies in the sample.

Table 3 shows percent inhibition in the presence and in the absence of a chaotropic agent (sodium chloride). While some COVID-19 samples show loss of neutralization effect in the presence of the chaotropic agent, other samples show no effect. Collectively, these results indicate the presence of high avidity antibodies that are not impacted by 1M sodium chloride. The determination of high avidity antibodies in a biological sample can provide additional diagnostic certainty in differentiating protective and/or sterilizing antibodies.

added to the beads and incubated with the population of beads. After a period of incubation, the 1 M NaCl and antibody (low avidity antibody) displaced during the incubation period are removed from the population of beads and the population of beads can be washed with a buffer. Biotinylated antibody specific for human immunoglobulin (anti-IgA, anti-IgM, anti-IgG, anti-kappa chain, and/or anti-lambda chain antibody) is added to the washed beads and incubated. Unbound biotinylated anti-human antibody is then washed away and labeled streptavidin-PE (Phycoerythrin) is added. The reaction is incubated and then washed prior to detection using a Bio-Plex 2200, Bio-Plex 200 or Luminex LX-200 platform. The sample fluorescence intensity is compared to the fluorescence intensity of a set of standards or calibrators to generate the relative fluorescence intensity (RFI) and, subsequently, a qualitative, semi-quantitative or quantitative result. A lack of signal for a particular subpopulation of beads onto which a SARS-CoV-2 spike protein (or fragment thereof) or a SARS-CoV-2 spike protein variant or fragment thereof has been immobilized indicates that low avidity neutralizing antibodies and/or no neutralizing antibodies to that SARS-CoV-2 spike protein variant or fragment thereof are present in the sample. The presence of a signal for a particular subpopulation of beads onto which a SARS-CoV-2 spike protein variant or fragment

TABLE 3

| | BioPlex Neutralization Assay | | | | | |
|---|---|---|---|---|---|---|
| | BioPlex seology IgG assay | | RBD (% Inhibition) (c/o: 20%) | | S1 (% Inhibition) (c/o: 14%) | | |
| Sample ID | RBD (AI) | S1 (AI) | High salt | Low Salt | High salt | Low Salt | Notes |
| CV2QS103 | 95.0 | 64.3 | 5% | 55% | 6% | 49% | Inhibition of Neutralization |
| CV2QS119 | 115.9 | 70.9 | 0% | 21% | 0% | 17% | by high salt |
| CV2QS128 | 96.5 | 52.2 | 17% | 25% | 12% | 21% | (Probably-Low avidity Ab) |
| CV2QS160 | 86.2 | 32.9 | 11% | 28% | 11% | 17% | |
| CV2QS186 | 95.5 | 65.1 | 13% | 40% | 17% | 36% | |
| CV2QS117 | 407.4 | 287.0 | 21% | 72% | 24% | 69% | Neutralization reduced |
| CV2QS135 | 362.9 | 251.6 | 25% | 43% | 32% | 44% | appreciably by high salt (Probably-Low avidity Ab) Note: High analyte specific IgG Ab |
| CV2QS101 | 277.9 | 222.6 | 73% | 84% | 71% | 82% | No effect of high salt on |
| CV2QS126 | 322.3 | 209.8 | 62% | 56% | 57% | 53% | neutralization |
| CV2QS142 | 267.7 | 259.9 | 56% | 55% | 55% | 55% | (Probably-High avidity antibody) |
| CV2QS110 | 202.3 | 247.6 | 48% | 40% | 47% | 42% | |
| CV2QS151 | 85.3 | 45.8 | 5% | 3% | 6% | 6% | No neutralizing Ab present |
| CV2QS152 | 101.6 | 67.7 | 0% | 11% | 0% | 7% | despite low to moderate |
| CV2QS149 | 77.3 | 39.7 | 0% | 0% | 0% | 0% | levels of serology |
| CV2QS159 | 77.8 | 43.8 | 0% | 0% | 0% | 0% | IgG antibodies |
| CV2QS165 | 39.9 | 18.6 | 0% | 0% | 0% | 0% | |
| CV2QS108 | 34.1 | 32.2 | 0% | 0% | 0% | 0% | |
| CV2QS124 | 21.7 | 10.6 | 0% | 0% | 0% | 0% | |
| CV2QS109 | 44.6 | 22.9 | 0% | 0% | 0% | 0% | |
| CV2QS133 | 54.0 | 31.0 | 0% | 0% | 0% | 0% | |

Example 7—Multiplex Detection of High Avidity Neutralizing Antibodies Specific for SARS-CoV-2 Spike Protein Variants or Fragments Thereof A population of fluorescently labeled beads comprising a plurality of subpopulations of fluorescently labeled beads to which individual SARS-CoV-2 spike protein variants or fragments thereof are immobilized is contacted with a patient sample, e.g., a biological sample from an individual suspected of having been exposed to SARS-CoV-2 or a subject immunized with a vaccine comprising SARS-CoV-2 spike protein along with a sample diluent. Unbound sample is removed from the population of beads and the population of beads can be washed with a buffer. 1 M NaCl is then thereof has been immobilized indicates that there are high avidity neutralizing antibodies in the sample and the amount of the high avidity neutralizing antibody can also be quantified. For example, the sample fluorescence intensity can be compared to the fluorescence intensity of a set of standards or calibrators to generate a qualitative, semi-quantitative or quantitative result for the amount of high avidity neutralizing antibody present in the sample.

Example 8—Singleplex Detection of Neutralizing Antibodies Specific for a SARS-CoV-2 Spike Protein Variant or Fragment Thereof A population of fluorescently labeled beads to which an individual SARS-CoV-2 spike protein, spike protein variant or fragment thereof is immobilized is contacted with a patient sample, e.g., a biological sample from an individual suspected of having been exposed to SARS-CoV-2 or a subject immunized with a vaccine comprising SARS-CoV2 spike protein along with a sample diluent. After incubation unbound sample is washed away and biotinylated human ACE2 receptor is added to the washed beads and incubated. The reaction is incubated and then washed and streptavidin-PE is added to the washed population of beads and incubated. After incubation, the population of beads is washed prior to detection using a Bio-Plex 2200, Bio-Plex 200 or Luminex LX-200 platform. The sample fluorescence intensity is compared to the fluorescence intensity of a set of standards or calibrators to generate the relative fluorescence intensity (RFI) and, subsequently, a qualitative, semi-quantitative or quantitative result. A lack of signal or a reduced signal (relative to a set of standards or calibrators) indicates that a neutralizing antibody to that SARS-CoV-2 spike protein variant or fragment thereof is present in the sample.

Example 9—Singleplex Detection of Neutralizing Antibodies Specific for a SARS-CoV-2 Spike Protein Variant or Fragment Thereof A population of fluorescently labeled beads to which an individual SARS-CoV-2 spike protein, spike protein variant or fragment thereof is immobilized is contacted with a patient sample, e.g., a biological sample from an individual suspected of having been exposed to SARS-CoV-2 or a subject immunized with a vaccine comprising SARS-CoV2 spike protein along with a sample diluent. After incubation unbound sample is washed away. A biotinylated fusion protein comprising human ACE2 receptor fused to an immunoglobulin Fc domain (a hACE2R-Fc fusion protein biotinylated on the Fc domain) is added to the washed beads and incubated. The reaction is incubated and then washed and streptavidin-PE is added to the washed population of beads and incubated. After incubation, the population of beads is washed prior to detection using a Bio-Plex 2200, Bio-Plex 200 or Luminex LX-200 platform. The sample fluorescence intensity is compared to the fluorescence intensity of a set of standards or calibrators to generate the relative fluorescence intensity (RFI) and, subsequently, a qualitative, semi-quantitative or quantitative result. A lack of signal or a reduced signal (relative to a set of standards or calibrators) indicates that a neutralizing antibody to that SARS-CoV-2 spike protein variant or fragment thereof is present in the sample.

Example 10—SARS-CoV2 Neutralizing Antibody Assay—Specificity

A total of 583 samples comprising 483 hospital normal (sample from subjects undergoing routine checkups) and 100 samples from pregnant women were tested for anti SARS-COV2 neutralizing and IgG antibodies. All samples tested were acquired before November 2019. nAb (neutralizing antibody) assay testing was performed in the presence of high and low salt to detect high and low avidity antibodies, respectively. The percentages provided in Table 4 refer the percentage of samples that did not contain neutralizing antibodies or IgG specific for the SARS-Cov-2 antigens.

TABLE 4

| Sample population | N | RBD-HS | S1-HS | RBD-LS | S1-LS | RBD IgG | S1 IgG |
|---|---|---|---|---|---|---|---|
| Hospital normals | 483 | 99.4% | 99.4% | 99.6% | 99.8% | 99.8% | 100.0% |
| Pregnant | 100 | 100.0% | 100.0% | 98.0% | 99.0% | 100.0% | 100.0% |

HS: High salt (1M NaCl);
LS: Low Salt (0.15M NaCl)
nAb cutoff: 0.35 ug/mL;
Serology IgG assay cutoff: 10 U/mL Example 11—SARS-CoV2 Neutralizing Antibody Assay—Cross Reactivity Analytical specificity of a serology test is a measure of its ability to identify specific antibodies while excluding other non-specific antibodies. Cross-reactivity refers to the ability of a ligand to support binding of antibodies other than those intended to be measured and cause false positive test results. 283 samples collected from 32 diseased groups were tested for cross reactivity in the nAb and a serology IgG assay. The list shows cross reactivity for only two analytes; RBD and S1. nAb assay was performed in the presence of high (1 M NaCl) and low salt (0.15 M NaCl) to detect high and low avidity antibodies respectively.

TABLE 5

| Cross reactants | N | RBD-HS | S1-HS | RBD-LS | S1-LS | RBD IgG | S1 IgG |
|---|---|---|---|---|---|---|---|
| SARS IgG | 5 | 0 | 0 | 1 | 0 | 0 | 0 |
| MERS IgG Pos | 5 | 0 | 0 | 0 | 0 | 0 | 0 |
| Influenza A | 14 | 0 | 1 | 1 | 1 | 0 | 0 |
| Influenza B | 9 | 0 | 0 | 0 | 0 | 0 | 0 |
| Common Cold | 9 | 0 | 0 | 0 | 0 | 0 | 0 |
| Flu Vaccinated | 7 | 0 | 0 | 0 | 0 | 0 | 0 |
| 2008 Flu Vaccine BioAssay validation panel | 36 | 0 | 0 | 0 | 0 | 0 | 0 |
| Haemophilus influenza Ab | 5 | 0 | 0 | 0 | 0 | 0 | 0 |
| Parainfluenza virus Ab Type I | 4 | 0 | 0 | 0 | 0 | 0 | 0 |
| Parainfluenza virus Ab Type III | 2 | 0 | 0 | 0 | 0 | 0 | 0 |
| Metapneumovirus (HMPV) IgG Pos | 5 | 0 | 0 | 0 | 0 | 0 | 0 |
| Rhinovirus IgG | 5 | 0 | 0 | 0 | 0 | 0 | 0 |
| *Streptococcus* Pneumonia Immunity Control | 1 | 0 | 0 | 0 | 0 | 0 | 0 |

TABLE 5-continued

| Cross reactants | N | RBD-HS | S1-HS | RBD-LS | S1-LS | RBD IgG | S1 IgG |
|---|---|---|---|---|---|---|---|
| CMV IgG Pos | 1 | 0 | 0 | 0 | 0 | 0 | 0 |
| EBV VCA IgG Pos | 23 | 0 | 0 | 0 | 0 | 0 | 0 |
| Measles IgG Pos | 13 | 0 | 0 | 0 | 0 | 0 | 0 |
| MMRV IgG Pos | 1 | 0 | 0 | 0 | 0 | 0 | 0 |
| Mumps IgG Pos | 14 | 0 | 0 | 1 | 1 | 0 | 0 |
| Rubella IgG Pos | 6 | 0 | 0 | 2 | 1 | 0 | 0 |
| VZV IgG Pos | 2 | 0 | 0 | 0 | 0 | 0 | 0 |
| HCV Ab Pos | 14 | 0 | 0 | 0 | 0 | 0 | 0 |
| Hepatitis A IgG Pos | 20 | 1 | 1 | 0 | 0 | 0 | 0 |
| Hepatitis B Pos Ab | 21 | 0 | 0 | 0 | 0 | 0 | 0 |
| Toxo IgG Pos | 1 | 0 | 0 | 0 | 0 | 0 | 0 |
| Syphilis IgG Pos | 2 | 0 | 0 | 0 | 0 | 0 | 0 |
| Elevated IgG | 1 | 0 | 0 | 0 | 0 | 1 | 0 |
| RF | 47 | 0 | 0 | 1 | 1 | 0 | 0 |
| ANA Positive | 4 | 0 | 0 | 0 | 0 | 0 | 1 |
| dsDNA Pos | 2 | 1 | 1 | 0 | 0 | 1 | 0 |
| Jo-1 Pos | 1 | 0 | 0 | 0 | 0 | 0 | 0 |
| RNP Pos | 1 | 0 | 0 | 0 | 0 | 0 | 0 |
| Sm Pos | 2 | 0 | 0 | 0 | 0 | 0 | 0 |
| Overall | 283 | 2 | 3 | 6 | 4 | 2 | 1 |

Example 12—SARS-CoV2 Neutralizing Antibody Assay—Positivity Rate 578 unique samples from COVID patients were procured from commercial vendors. Of the 578 samples, 453 (78.4%) came with complete demographics and PCR test results. All samples were tested by the BioPlex 2200 serology IgG assay and neutralizing antibody (nAb) assay. While serology IgG data was collected for all four analytes (RBD, S1, S2 and N), the following table shows data for RBD and S1 analytes only. Testing for the presence of high and low avidity nAb was performed with RBD and S1 coupled beads only. High avidity antibodies were detected in the presence of 1M sodium chloride (HS) and 0.15 M NaCL (LS).

TABLE 6

Number of positive samples exhibiting IgG and neutralizing antibodies

| Days post symptom onset | | # of Positive samples | | | | | |
|---|---|---|---|---|---|---|---|
| | | CoV-2 nAb-HS | | CoV-2 nAb-LS | | BioPlex CoV-2 IgG | |
| | N | RBD-HS | S1-HS | RBD-LS | S1-LS | RBD IgG | S1 IgG |
| ≤7 | 78 | 53 | 48 | 59 | 56 | 59 | 57 |
| 8-14 | 67 | 53 | 49 | 54 | 50 | 55 | 53 |
| 15-30 | 124 | 97 | 85 | 110 | 102 | 112 | 109 |
| 31-60 | 226 | 190 | 169 | 203 | 198 | 212 | 209 |
| >60 | 83 | 67 | 64 | 69 | 67 | 75 | 74 |

TABLE 7

Percent positive samples exhibiting IgG and neutralizing antibodies

| Days post symptom | | CoV-2 nAb-HS | | CoV-2 nAb-LS | | BioPlex CoV-2 IgG | |
|---|---|---|---|---|---|---|---|
| | N | RBD-HS | S1-HS | RBD-LS | S1-LS | RBD IgG | S1 IgG |
| ≤7 | 78 | 68% | 62% | 76% | 72% | 76% | 73% |
| 8-14 | 67 | 79% | 73% | 81% | 75% | 82% | 79% |
| 15-30 | 124 | 78% | 69% | 89% | 82% | 90% | 88% |
| 31-60 | 226 | 84% | 75% | 90% | 88% | 94% | 92% |
| >60 | 83 | 81% | 77% | 83% | 81% | 90% | 89% |

Example 13—SARS-CoV2 Neutralizing Antibody Assay—Concordance

For methodology comparison, the BioPlex 2200 neutralizing antibody assay was compared to a serologic IgG assay and the clinical status of the sample. Clinical status was established based on clinical findings coupled with the PCR test result. While negative agreements (% NA) are comparable between the nAb (neutralizing antibody), serology IgG and the clinical status irrespective of the avidity status, positive agreements (% PA) shows better correlation between the nAb, serology IgG and clinical status in the presence of low salt. Low salt (LS) refers to 0.15 M NaCl and high salt (HS) refers to 1 M NaCl). Negative agreement remained constant at low and high salt. However, positive agreement did not. This lends credence to the hypothesis that the antibody status does not predict the potency of neutralization.

TABLE 8

| | | Neutralizing antibody | | | | | | | |
|---|---|---|---|---|---|---|---|---|---|
| | | RBD-HS | | | | RBD-LS | | | |
| | | Pos | Neg | PA (%) | NA (%) | Pos | Neg | PA (%) | NA (%) |
| Clinical Status | Pos | 460 | 118 | 79.6 | 99.4 | 495 | 83 | 85.6 | 98.8 |
| | Neg | 5 | 861 | (76.1-82.7) | (98.7-99.8) | 10 | 856 | (82.5-88.3) | (97.9-99.4) |
| BioPlex anti-RBD IgG | Pos | 512 | 76 | 87.1 | 98.6 | 556 | 32 | 94.6 | 98.0 |
| | Neg | 13 | 939 | (84.1-89.5) | (97.7-99.2) | 19 | 933 | (92.4-96.1) | (96.9-98.7) |

TABLE 8-continued

|  |  | S1-1-HS | | | | S1-LS | | | |
| --- | --- | --- | --- | --- | --- | --- | --- | --- | --- |
|  |  | Pos | Neg | PA (%) | NA (%) | Pos | Neg | PA (%) | NA (%) |
| Clinical | Pos | 415 | 163 | 71.8 | 99.3 | 473 | 105 | 81.8 | 99.3 |
| Status | Neg | 6 | 860 | (68.0-75.3) | (98.5-99.7) | 6 | 860 | (78.5-84.8) | (98.5-99.7) |
| BioPlex | Pos | 467 | 104 | 81.8 | 99.1 | 556 | 32 | 91.9 | 98.6 |
| anti-S1 IgG | Neg | 9 | 960 | (78.4-84.7) | (98.2-99.5) | 19 | 933 | (89.4-93.9) | (97.6-99.1) |

Figure 5A:
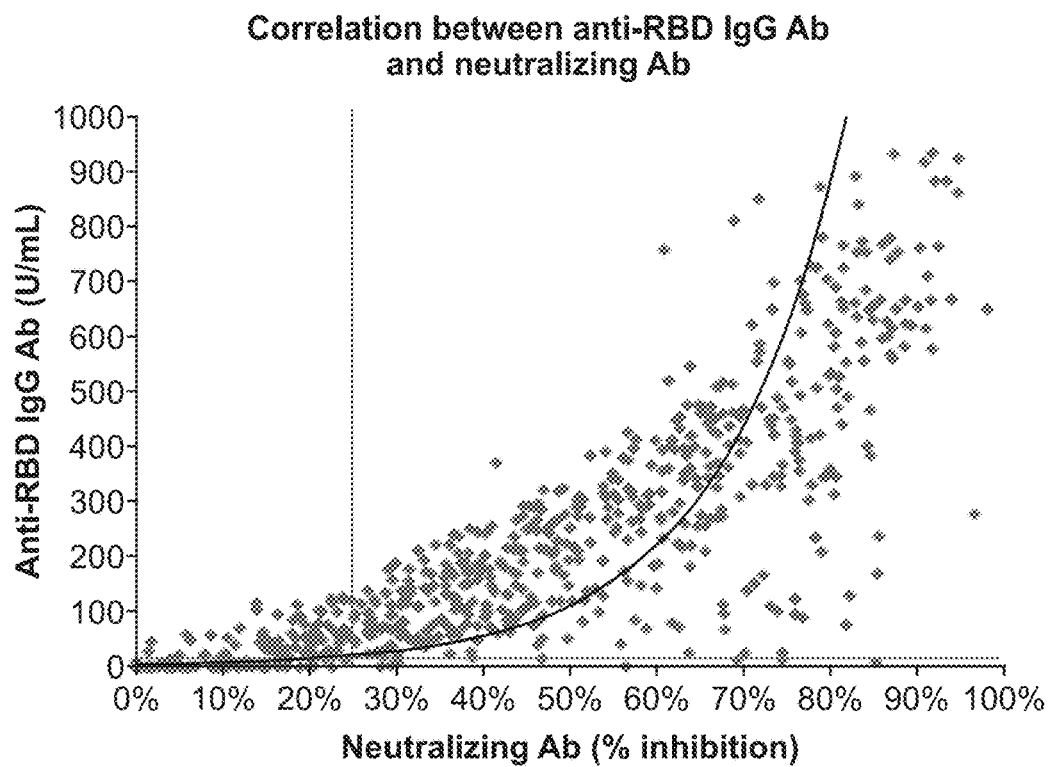
FIGS. 5A and 5B demonstrate the correlation between anti-RBD binding IgG antibody and neutralizing antibody.
Figure 5B:
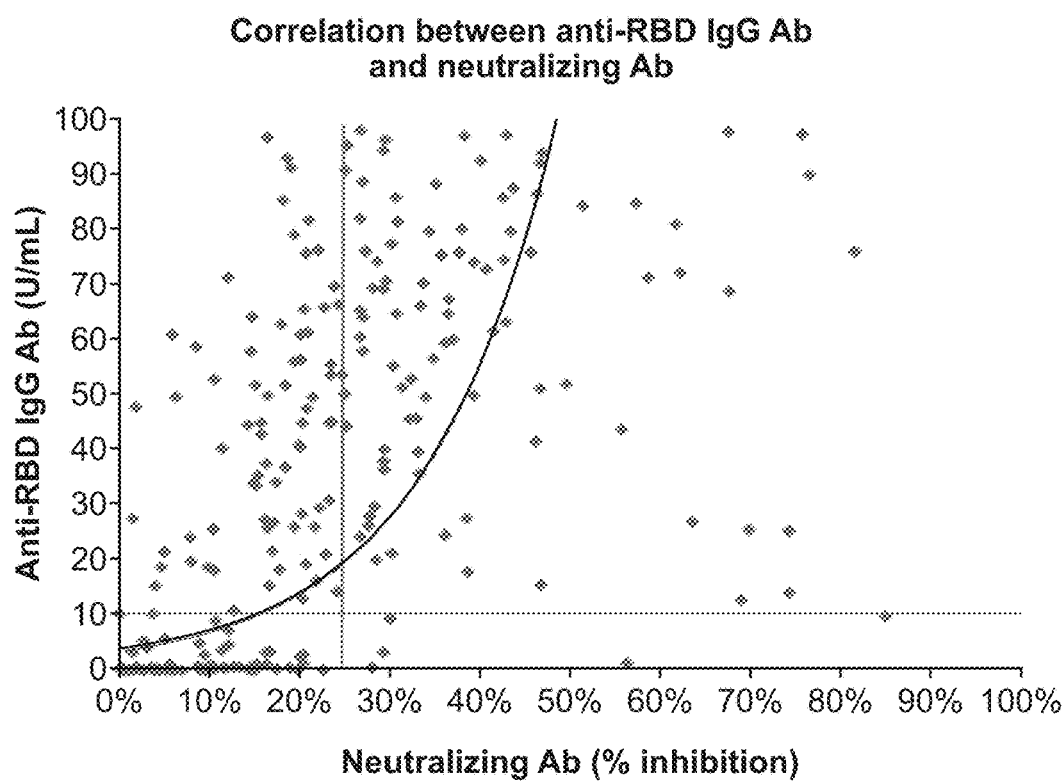
Figure 6:
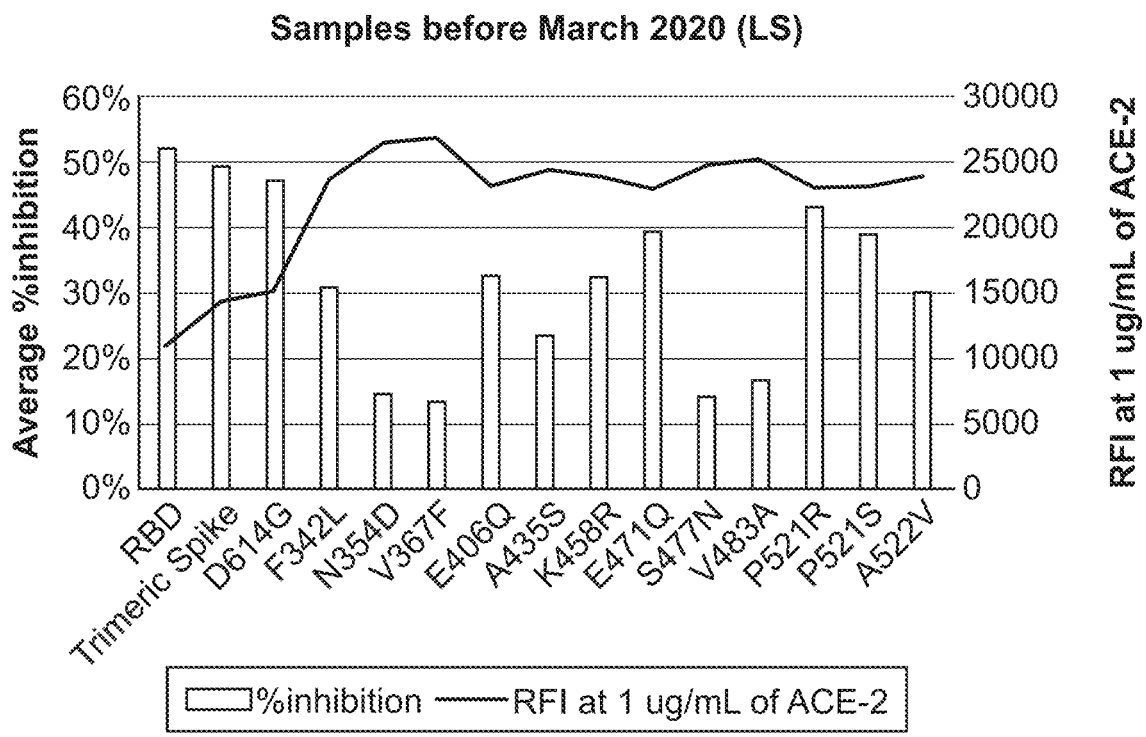
FIGS. 6-9 illustrate neutralizing antibodies present in samples for various mutants under low salt conditions (LS=0.15 M NaCl, FIGS. 6 and 7) and high salt conditions (HS=1 M NaCl, FIGS. 8 and 9) for samples obtained before March 2020 and after June 2020.
Figure 7:
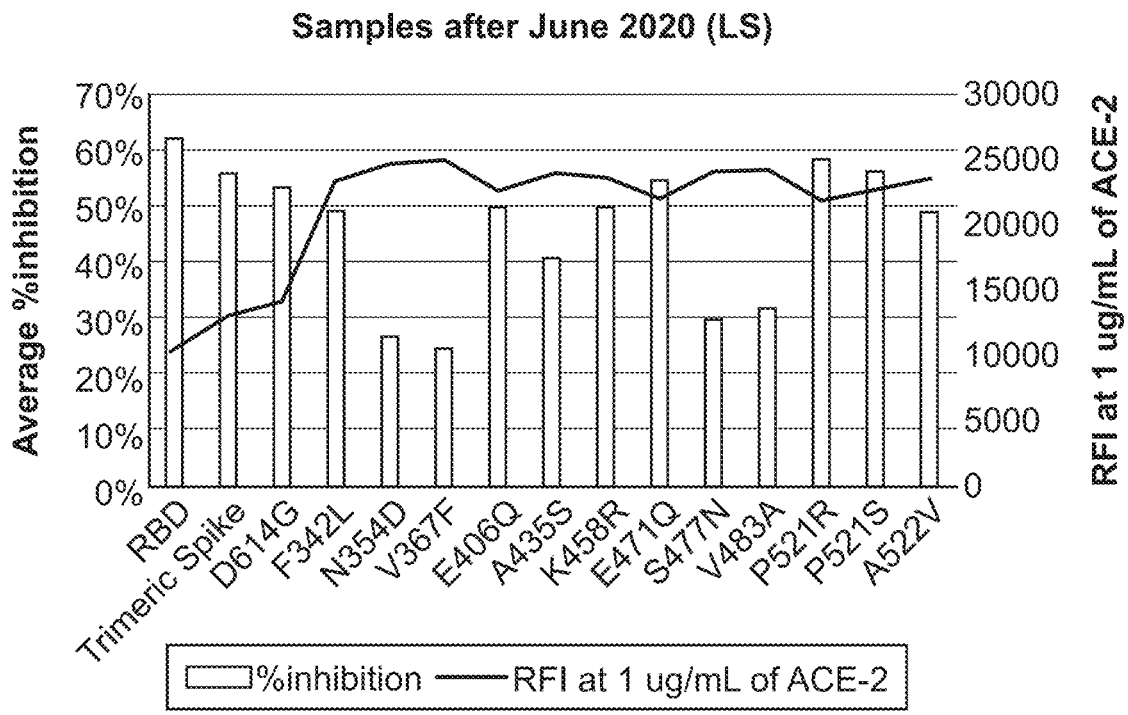
Figure 8:
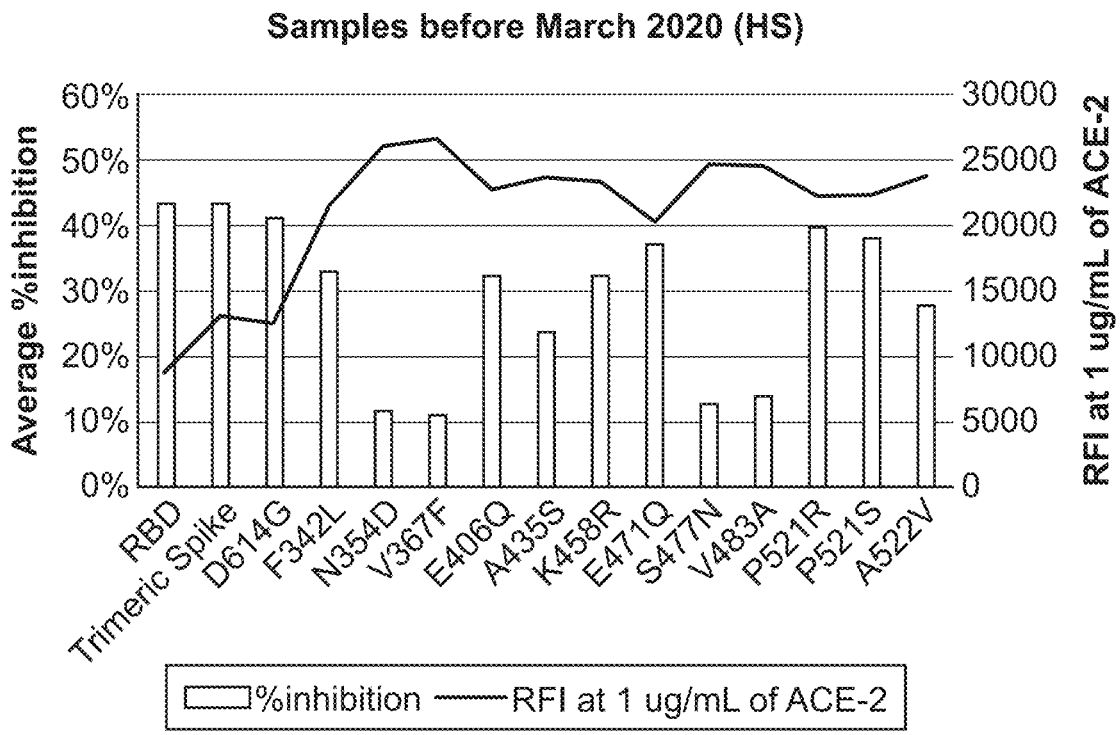
Figure 9:
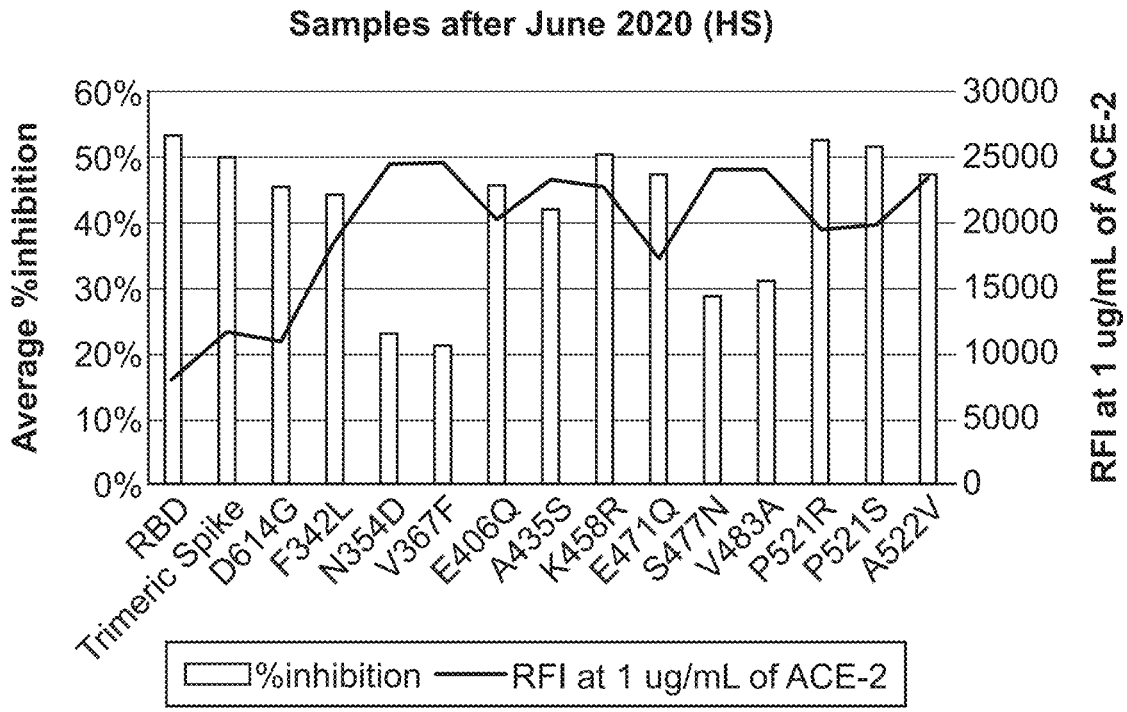
Figure 10:
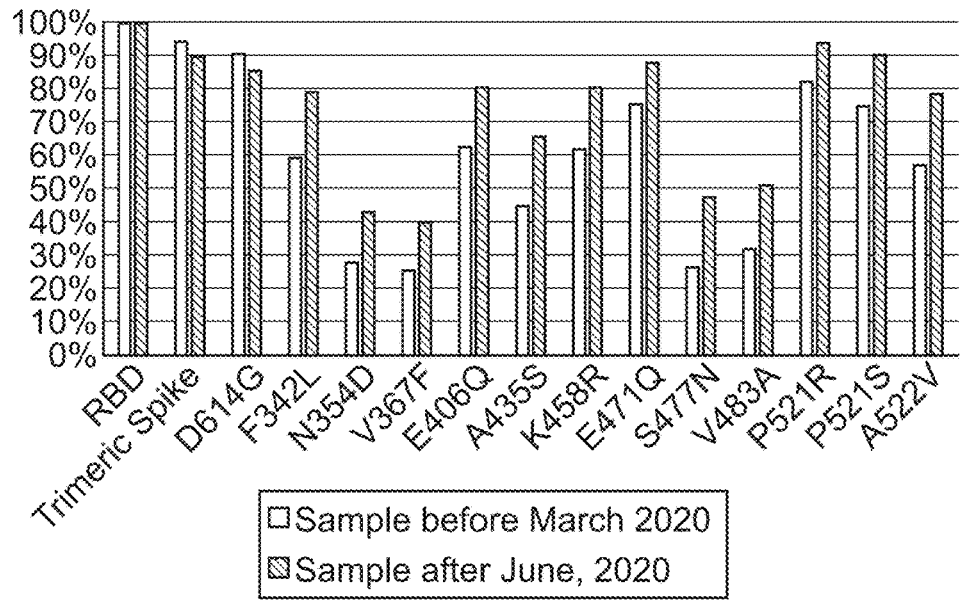
FIGS. 10-11 illustrate antibody mediated inhibition after normalization to 100% of the wild type. RBD mutants demonstrated differential nAb response for samples collected before and after June 2020.
Figure 11:
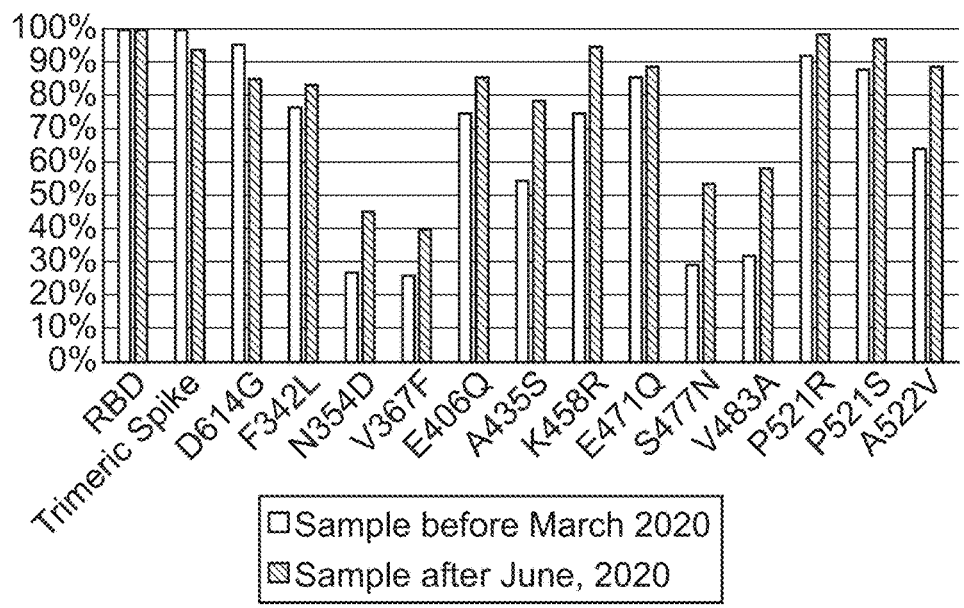

Example 14—SARS-CoV2 Neutralizing Antibody Assay—Correlation with the Serology Anti-RBD IgG Assay 675 COVID19 patient serum samples were tested on both SARS-CoV-2 serology IgG assay and neutralizing antibody assay. Among 675 patients, 453 were confirmed by PCR positive test results. The test results demonstrated the correlation between anti-RBD binding IgG antibody and neutralizing antibody. However, approximately 5% of the samples exhibit high serology IgG and low nAb response or vice versa as shown in FIGS. 5A and 5B.

Example 15—SARS-CoV2 Neutralizing Antibody Assay—Earlier Infected Patient Samples Lack Neutralizing Effects on Some of RBD Mutants Twelve RBD mutants (F342L, N354D, V36F, E406Q, A435S, K458R, E471Q, S477N, V483A, P521R, P521S, and A522V) as well as wild type RBD, whole trimeric spike protein and the dominant pandemic mutant form D614G were tested in the neutralizing antibody assay. All RBD mutants demonstrate higher binding ability to ACE-2 receptor compared to wild type RBD, Trimeric spike protein and the D614G S1 mutant. The COVID19 patient serum samples demonstrated significantly lower inhibition on four RBD mutants—N354D, V367F, S477N and V483A, especially in earlier SARS-CoV2 infected patients (see Table 9 and FIGS. 6-11).

TABLE 9

| | Recombinant protein vendor | Icosagen RBD WT sequence | Icosagen Trimeric Spike Protein | Sino Bio S1 mutant D614G | Sino Bio RBD mutant F342L | Sino Bio RBD mutant N354D | Sino Bio RBD mutant V367F | Sino Bio RBD mutant E406Q | Sino Bio RBD mutant A435S | Sino Bio RBD mutant K458R | Sino Bio RBD mutant E471Q | Sino Bio RBD mutant S477N | Sino Bio RBD mutant V483A | Sino Bio RBD mutant P521R | Sino Bio RBD mutant P521S | Sino Bio RBD mutant A522V |
|---|---|---|---|---|---|---|---|---|---|---|---|---|---|---|---|---|
| | | | | | | | | LS | | | | | | | | |
| Samples collected before March (n = 30) | Ave % inhibition | 52% | 49% | 47% | 31% | 14% | 13% | 32% | 23% | 32% | 39% | 14% | 17% | 43% | 39% | 30% |
| | RFI at 1 ug/mL of ACE-2 | 10862 | 14268 | 15020 | 23526 | 26476 | 26833 | 23025 | 24298 | 23811 | 22841 | 24731 | 25144 | 22946 | 23065 | 23839 |
| | Normalized % inhibition to WT RBD | 100% | 94% | 90% | 59% | 28% | 25% | 62% | 45% | 62% | 75% | 26% | 32% | 83% | 75% | 57% |
| | | | | | | | | HS | | | | | | | | |
| | Ave % inhibition | 43% | 43% | 41% | 33% | 12% | 11% | 32% | 24% | 32% | 37% | 13% | 14% | 40% | 38% | 28% |
| | RFI at 1 ug/mL of ACE-2 | 8648 | 13133 | 12517 | 21304 | 25954 | 26574 | 22642 | 23606 | 23210 | 20150 | 24541 | 24438 | 22109 | 22248 | 23670 |
| | Normalized % inhibition to WT RBD | 100% | 100% | 95% | 77% | 27% | 26% | 75% | 55% | 75% | 86% | 29% | 32% | 92% | 88% | 64% |

| | | LS | | | | | | | | | | | | | | |
|---|---|---|---|---|---|---|---|---|---|---|---|---|---|---|---|---|
| | | RBD WT sequence | Trimeric Spike Protein | S1 mutant D614G | RBD mutant F342L | RBD mutant N354D | RBD mutant V367F | RBD mutant E406Q | RBD mutant A435S | RBD mutant K458R | RBD mutant E471Q | RBD mutant S477N | RBD mutant V483A | RBD mutant P521R | RBD mutant P521S | RBD mutant A522V |
| Samples collected after June (n = 30) | Ave % inhibition | 62% | 56% | 53% | 49% | 27% | 25% | 50% | 41% | 50% | 54% | 30% | 32% | 58% | 56% | 49% |
| | RFI at 1 ug/mL of ACE-2 | 10398 | 13143 | 14009 | 23324 | 24678 | 24927 | 22583 | 23888 | 23547 | 21939 | 24104 | 24222 | 21772 | 22730 | 23614 |
| | Normalized % inhibition to WT RBD | 100% | 90% | 85% | 79% | 43% | 40% | 80% | 65% | 80% | 88% | 48% | 51% | 94% | 90% | 79% |
| | | | | | | | | HS | | | | | | | | |
| | Ave % inhibition | 53% | 50% | 45% | 44% | 24% | 21% | 45% | 42% | 50% | 47% | 29% | 31% | 52% | 52% | 47% |
| | RFI at 1 ug/mL of ACE-2 | 7956 | 11658 | 10858 | 18445 | 24401 | 24510 | 20096 | 23230 | 22633 | 17146 | 23893 | 23982 | 19464 | 19819 | 23273 |
| | Normalized % inhibition to WT RBD | 100% | 94% | 85% | 83% | 45% | 40% | 85% | 79% | 95% | 89% | 54% | 58% | 99% | 97% | 89% |

FIGS. 6-9 illustrate neutralizing antibodies present in samples for various mutants under low salt conditions (LS=0.15 M NaCl, FIGS. 6 and 7) and high salt conditions (HS=1 M NaCl, FIGS. 8 and 9) for samples obtained before March 2020 and after June 2020. When antibody mediated inhibition was normalized to 100% of the wild type, RBD mutants demonstrated differential nAb response for samples collected before and after June 2020 (FIG. 10, low salt conditions and FIG. 11, high salt conditions). While high salt showed slightly elevated inhibition, the response pattern looked similar. Low salt conditions were 0.15 M NaCl and high salt conditions were 1 M NaCl.

REFERENCES

1. Cheng Z J and Shan J. 2019 Novel coronavirus: where we are and what we know. Infection. 2020, April 48(2): 155-163. doi: 10.1007/s15010-020-01401-y.
2. Cui J, Li F, and Shi Z L. Origin and evolution of pathogenic coronaviruses. Nature Reviews. 2020, Mar. 17: 181-192. doi: 10.1038/s41579-018-0118-9.
3. He F, Deng Y, Li W. Coronavirus disease 2019: What we know? Journal of Medical Virology. 2020, Mar. 14. doi: 10.1002/jmv.25766.
4. Guo L, Ren L, Yang S et al. Profiling Early Humoral Response to Diagnose Novel Coronavirus Disease (COVID-19). Clinical Infectious Disease. 2020, Mar. 21, pii: ciaa310. doi: 10.1093/cid/ciaa310.
5. Weiss S R and Navas-Martin S. Coronavirus Pathogenesis and the Emerging Pathogen Severe Acute Respiratory Syndrome Coronavirus. Microbiology and molecular biology reviews. 2005, December 69 (4): 635-664. doi: 10.1128/MMBR.69.4.635-664.2005.
6. Zhang W, Du R H, Li B, et al. Molecular and serological investigation of 2019-nCoV infected patients: implication of multiple shedding routes. Emerging Microbes & Infections. 2020, 9:1, 386-389. doi: 10.1080/22221751.2020.1729071.
7. Zhao J, Yuan Q, Wang H, et al. Antibody responses to SARS-CoV-2 in patients of novel coronavirus disease 2019. Clinical Infectious Disease. 2020, Mar. 28, pii: ciaa344. doi: 10.1093/cid/ciaa344 13 [EN].
8. Zhou P, Yang X L, Wang X G, et al. A pneumonia outbreak associated with a new coronavirus of probable bat origin. Nature. 2020, March 579 (7798): 270-273. doi: 10.1038/s41586-020-2012-7.
9. Fan Wu, Aojie Wang, Mei Liu, et al. Neutralizing antibody responses to SARS-CoV-2 in a COVID-19 recovered patient cohort and their implications. 2020 Apr. 29 doi: doi.org/10.1101/2020.03.30.20047365.
10. Juanjuan Zhao, Quan Yuan, Haiyan Wang, et al. Antibody responses to SARS-CoV-2 in patients of novel coronavirus disease 2019. 2020 Mar. 3 doi: doi.org/10.1101/2020.03.02.20030189.

We claim:
1. A substrate comprising a population of particles or beads comprising two or more separate subpopulations of particles or beads, each subpopulation of particles or beads being distinguishable by a specific detectable parameter and each subpopulation of beads comprising a distinct SARS-CoV-2 spike protein variant or fragment thereof immobilized thereon and, optionally, a further subpopulation of beads comprising a SARS-CoV-2 spike protein or fragment thereof immobilized thereon.

2. The substrate according to claim 1, wherein said substrate is glass, plastic, polystyrene or nitrocellulose.

3. The substrate according to claim 1, wherein said population comprises two or more separate subpopulations of particles or beads selected from:
  a) a SARS-CoV-2 spike protein variant or fragment thereof containing the mutation V367X immobilized on a first particle or bead having a first specific detectable physical parameter, where X is any amino acid or X is F;
  b) a SARS-CoV-2 spike protein variant or fragment thereof containing the mutation F342X immobilized on a second particle or bead having a second specific detectable physical parameter, where X is any amino acid or X is L;
  c) a SARS-CoV-2 spike protein variant or fragment thereof containing the mutation A435X immobilized on a third particle or bead having a third specific detectable physical parameter, where X is any amino acid or X is S;
  d) a SARS-CoV-2 spike protein variant or fragment thereof containing the mutation K458X immobilized on a fourth particle or bead having a fourth specific detectable physical parameter, where X is any amino acid or X is R;
  e) a SARS-CoV-2 spike protein variant or fragment thereof containing the mutation V483X immobilized on a fifth particle or bead having a fifth specific detectable physical parameter, where X is any amino acid or X is A;
  f) a SARS-CoV-2 spike protein variant or fragment thereof containing the mutation V483X immobilized on a sixth particle or bead having a sixth specific detectable physical parameter, where X is any amino acid or X is A;
  g) a SARS-CoV-2 spike protein variant or fragment thereof containing the mutation N354X immobilized on a seventh particle or bead having a seventh specific detectable physical parameter, where X is any amino acid or X is D;
  h) a SARS-CoV-2 spike protein variant or fragment thereof containing the mutations R683X1 and/or R685X2 immobilized on an eighth particle or bead having an eighth specific detectable physical parameter, where X1 and X2 are any amino acid or X1 and X2 are A;
  i) a SARS-CoV-2 spike protein variant or fragment thereof containing the mutations K986X3 and/or V987X4 immobilized on a ninth particle or bead having a ninth specific detectable physical parameter, where X3 and X4 are any amino acid or X3 and X4 are P;
  j) a SARS-CoV-2 spike protein variant or fragment thereof containing the mutations R683X1, R685X2, K986X3, and V987X4 immobilized on a tenth particle or bead having a tenth specific detectable physical parameter, where X1 is any amino acid or X1 is A; X2 is any amino acid or X2 is A; X3 is any amino acid or X3 is P; and X4 is any amino acid or X4 is P; and
  k) a SARS-CoV-2 spike protein or fragment thereof immobilized on an eleventh particle or bead having an eleventh specific detectable physical parameter.

4. The substrate according to claim 3, wherein the specific detectable physical parameter is a fluorescent dye (fluorophore), luminescent agent, electron-dense reagent, radioisotope or particle size.

5. The substrate according to claim 4, wherein the specific detectable parameter is a fluorophore.

6. A method for detecting neutralizing and/or protective antibodies in a mammal comprising obtaining a biological sample from the mammal, contacting said biological sample with a substrate comprising a substrate according to claim 1 and detecting the presence or absence of neutralizing antibodies bound to SARS-CoV-2 spike protein variants or fragments thereof on the surface of said substrate.

7. The method according to claim 6, wherein the mammal is a human, non-human primate, canine, or feline.

8. The method according to claim 6, wherein the presence or absence of neutralizing antibodies comprises contacting the substrate with human ACE2 receptor and detecting the presence or absence of ACE2 receptor binding to substrate subpopulations onto which SARS-CoV-2 spike protein variants or fragments thereof have been immobilized, the detection of ACE2 receptor binding to a substrate subpopulation indicating a lack of neutralizing antibody specific for a specific a SARS-CoV-2 spike protein variant or fragment thereof.

9. The method according to claim 8, wherein ACE2 receptor binding to a substrate subpopulation is detected using an antibody specific for ACE2 receptor that is detectably labeled or an ACE2 receptor that is detectably labeled.

10. The method according to claim 6, wherein neutralizing antibody bound to a substrate comprising a given a SARS-CoV-2 spike protein variant or fragment thereof is detected using a species specific anti-immunoglobulin (Ig) antibody.

11. The method according to claim 6, said method further comprising detecting the presence, absence or amounts of cytokines selected from IL-1beta, IFN-γ, IFNγ-induced protein 10 (IP-10), monocyte chemoattractant protein 1 (MCP-1), IL-4, IL-10, IL-2R, IL-6, granulocyte colony-stimulating factor (G-CSF), macrophage inflammatory protein-1A, and TNF-α in said biological sample.

12. The method according to claim 11, wherein said one or more cytokine is selected from IL-6, IL-2R, granulocyte colony-stimulating factor, IP-10, MCP-1, macrophage inflammatory protein-1A, TNF-α, and combinations thereof.

13. A method for detecting high avidity neutralizing antibodies in a mammal comprising obtaining a biological sample from the mammal, contacting said biological sample with a substrate comprising a substrate according to claim 1 and detecting the presence or absence of high avidity neutralizing antibodies bound to SARS-CoV-2 spike protein variants or fragments thereof on the surface of said substrate.

14. The method according to claim 13, wherein the method comprises:
  a) contacting the substrate with the biological sample;
  b) optionally removing the biological sample from the substrate and washing the substrate to remove unbound material and antibody;
  c) contacting the substrate with one or more chaotropic agents;

d) removing the one or more chaotropic agents from the substrate;

e) optionally, washing the substrate; and f) detecting the presence or absence of high avidity neutralizing antibody binding to substrate subpopulations onto which SARS-CoV-2 spike protein or fragments thereof and SARS-CoV-2 spike protein variants or fragments thereof have been immobilized.

15. The method according to claim 14, wherein the chaotropic agent is sodium chloride, sodium thiocyanate, and/or urea.

16. The method according to claim 13, wherein the method comprises detecting SARS-CoV-2 spike protein or fragments thereof and/or SARS-CoV-2 spike protein variants or fragments thereof present on the substrate with an ACE2 receptor that is detectably labeled or with an antibody specific for the ACE2 receptor that is detectably labeled.

17. The method according to claim 13, wherein high avidity neutralizing antibody bound to a substrate comprising a given a SARS-CoV-2 spike protein or fragment thereof and/or a SARS-CoV-2 spike protein variant or fragment thereof is detected using a species specific anti-immunoglobulin (Ig) antibody, wherein the anti-Ig antibody is biotinylated and binding of said anti-IgG antibody to neutralizing antibody is detected with fluorophore labeled avidin or streptavidin or an anti-IgG antibody labeled with a fluorophore.

18. A method for detecting a neutralizing antibody in a mammal comprising obtaining a biological sample from the mammal, contacting said biological sample with a substrate according to claim 1 and detecting the presence or absence of a neutralizing antibody bound to a SARS-CoV-2 spike protein variant or fragment thereof on the surface of said substrate, said biological sample being obtained from individuals suspected of infection by the virus, treated with SARS-CoV-2 neutralizing antibodies or convalescent plasma, or immunized with a vaccine comprising the SARS-CoV2 spike protein.

19. The method according to claim 9, wherein the ACE2 receptor is a truncated or modified ACE2 receptor or is an ACE2 receptor fusion protein.

20. The method according to claim 19, wherein the ACE2 receptor fusion protein comprises an immunoglobulin Fc domain fused to the carboxyl-terminus of the ACE2 receptor.

21. The method according to claim 20, wherein the fusion protein is biotinylated on the Fc domain and is detected using streptavidin-PE.

* * * * *

SEQUENCE LISTING

```
<160> NUMBER OF SEQ ID NOS: 4

<210> SEQ ID NO 1
<211> LENGTH: 1273
<212> TYPE: PRT
<213> ORGANISM: Severe acute respiratory syndrome coronavirus 2
<220> FEATURE:
<221> NAME/KEY: MISC_FEATURE
<222> LOCATION: (342)..(342)
<223> OTHER INFORMATION: Xaa = any amino acid
<220> FEATURE:
<221> NAME/KEY: MISC_FEATURE
<222> LOCATION: (354)..(354)
<223> OTHER INFORMATION: Xaa = any amino acid
<220> FEATURE:
<221> NAME/KEY: MISC_FEATURE
<222> LOCATION: (367)..(367)
<223> OTHER INFORMATION: Xaa = any amino acid
<220> FEATURE:
<221> NAME/KEY: MISC_FEATURE
<222> LOCATION: (435)..(435)
<223> OTHER INFORMATION: Xaa = any amino acid
<220> FEATURE:
<221> NAME/KEY: MISC_FEATURE
<222> LOCATION: (458)..(458)
<223> OTHER INFORMATION: Xaa = any amino acid
<220> FEATURE:
<221> NAME/KEY: MISC_FEATURE
<222> LOCATION: (483)..(483)
<223> OTHER INFORMATION: Xaa = any amino acid
<220> FEATURE:
<221> NAME/KEY: MISC_FEATURE
<222> LOCATION: (683)..(683)
<223> OTHER INFORMATION: Xaa = any amino acid
<220> FEATURE:
<221> NAME/KEY: MISC_FEATURE
<222> LOCATION: (685)..(685)
<223> OTHER INFORMATION: Xaa = any amino acid
<220> FEATURE:
<221> NAME/KEY: MISC_FEATURE
<222> LOCATION: (986)..(987)
<223> OTHER INFORMATION: Xaa = any amino acid
```

<400> SEQUENCE: 1

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Xaa Asn Ala Thr Arg Phe Ala Ser Val Tyr Ala
            340                 345                 350

Trp Xaa Arg Lys Arg Ile Ser Asn Cys Val Ala Asp Tyr Ser Xaa Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415
```

```
Lys Ile Ala Asp Tyr Asn Tyr Lys Leu Pro Asp Asp Phe Thr Gly Cys
                420                 425                 430

Val Ile Xaa Trp Asn Ser Asn Leu Asp Ser Lys Val Gly Gly Asn
            435                 440                 445

Tyr Asn Tyr Leu Tyr Arg Leu Phe Arg Xaa Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Xaa Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Xaa Ala Xaa Ser Val Ala
    675                 680                 685

Ser Gln Ser Ile Ile Ala Tyr Thr Met Ser Leu Gly Ala Glu Asn Ser
690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
            770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830
```

```
Phe Ile Lys Gln Tyr Gly Asp Cys Leu Gly Asp Ile Ala Arg Asp
    835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
    915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Xaa Xaa Glu Ala Glu Val Gln
    980                 985                 990

Ile Asp Arg Leu Ile Thr Gly Arg Leu Gln Ser Leu Gln Thr Tyr Val
    995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
```

-continued

```
             1235                1240                1245
Ser Cys Gly Ser Cys Cys Lys Phe Asp Glu Asp Asp Ser Glu Pro
     1250                1255                1260

Val Leu Lys Gly Val Lys Leu His Tyr Thr
     1265                1270

<210> SEQ ID NO 2
<211> LENGTH: 1273
<212> TYPE: PRT
<213> ORGANISM: Severe acute respiratory syndrome coronavirus 2
<220> FEATURE:
<221> NAME/KEY: MISC_FEATURE
<222> LOCATION: (342)..(342)
<223> OTHER INFORMATION: Xaa = any amino acid
<220> FEATURE:
<221> NAME/KEY: MISC_FEATURE
<222> LOCATION: (354)..(354)
<223> OTHER INFORMATION: Xaa = any amino acid or Asx
<220> FEATURE:
<221> NAME/KEY: MISC_FEATURE
<222> LOCATION: (367)..(367)
<223> OTHER INFORMATION: Xaa = any amino acid
<220> FEATURE:
<221> NAME/KEY: MISC_FEATURE
<222> LOCATION: (435)..(435)
<223> OTHER INFORMATION: Xaa = any amino acid
<220> FEATURE:
<221> NAME/KEY: MISC_FEATURE
<222> LOCATION: (458)..(458)
<223> OTHER INFORMATION: Xaa = any amino acid
<220> FEATURE:
<221> NAME/KEY: MISC_FEATURE
<222> LOCATION: (483)..(483)
<223> OTHER INFORMATION: Xaa = any amino acid
<220> FEATURE:
<221> NAME/KEY: MISC_FEATURE
<222> LOCATION: (683)..(683)
<223> OTHER INFORMATION: Xaa = any amino acid
<220> FEATURE:
<221> NAME/KEY: MISC_FEATURE
<222> LOCATION: (685)..(685)
<223> OTHER INFORMATION: Xaa = any amino acid
<220> FEATURE:
<221> NAME/KEY: MISC_FEATURE
<222> LOCATION: (986)..(987)
<223> OTHER INFORMATION: Xaa = any amino acid

<400> SEQUENCE: 2

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140
```

```
Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Xaa Asn Ala Thr Arg Phe Ala Ser Val Tyr Ala
            340                 345                 350

Trp Xaa Arg Lys Arg Ile Ser Asn Cys Val Ala Asp Tyr Ser Xaa Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Xaa Trp Asn Ser Asn Asn Leu Asp Ser Lys Val Gly Gly Asn
        435                 440                 445

Tyr Asn Tyr Leu Tyr Arg Leu Phe Arg Xaa Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Xaa Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
```

```
                    565                 570                 575
Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Xaa Ala Xaa Ser Val Ala
            675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
            770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
            850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Xaa Xaa Glu Ala Glu Val Gln
            980                 985                 990
```

```
Ile Asp Arg Leu Ile Thr Gly Arg Leu Gln Ser Leu Gln Thr Tyr Val
        995                1000                1005

Thr Gln Gln Leu Ile Arg Ala Ala Glu Ile Arg Ala Ser Ala Asn
    1010               1015               1020

Leu Ala Ala Thr Lys Met Ser Glu Cys Val Leu Gly Gln Ser Lys
    1025               1030               1035

Arg Val Asp Phe Cys Gly Lys Gly Tyr His Leu Met Ser Phe Pro
    1040               1045               1050

Gln Ser Ala Pro His Gly Val Val Phe Leu His Val Thr Tyr Val
    1055               1060               1065

Pro Ala Gln Glu Lys Asn Phe Thr Thr Ala Pro Ala Ile Cys His
    1070               1075               1080

Asp Gly Lys Ala His Phe Pro Arg Glu Gly Val Phe Val Ser Asn
    1085               1090               1095

Gly Thr His Trp Phe Val Thr Gln Arg Asn Phe Tyr Glu Pro Gln
    1100               1105               1110

Ile Ile Thr Thr Asp Asn Thr Phe Val Ser Gly Asn Cys Asp Val
    1115               1120               1125

Val Ile Gly Ile Val Asn Asn Thr Val Tyr Asp Pro Leu Gln Pro
    1130               1135               1140

Glu Leu Asp Ser Phe Lys Glu Glu Leu Asp Lys Tyr Phe Lys Asn
    1145               1150               1155

His Thr Ser Pro Asp Val Asp Leu Gly Asp Ile Ser Gly Ile Asn
    1160               1165               1170

Ala Ser Val Val Asn Ile Gln Lys Glu Ile Asp Arg Leu Asn Glu
    1175               1180               1185

Val Ala Lys Asn Leu Asn Glu Ser Leu Ile Asp Leu Gln Glu Leu
    1190               1195               1200

Gly Lys Tyr Glu Gln Tyr Ile Lys Trp Pro Trp Tyr Ile Trp Leu
    1205               1210               1215

Gly Phe Ile Ala Gly Leu Ile Ala Ile Val Met Val Thr Ile Met
    1220               1225               1230

Leu Cys Cys Met Thr Ser Cys Cys Ser Cys Leu Lys Gly Cys Cys
    1235               1240               1245

Ser Cys Gly Ser Cys Cys Lys Phe Asp Glu Asp Ser Glu Pro
    1250               1255               1260

Val Leu Lys Gly Val Lys Leu His Tyr Thr
    1265               1270

<210> SEQ ID NO 3
<211> LENGTH: 1273
<212> TYPE: PRT
<213> ORGANISM: Severe acute respiratory syndrome coronavirus 2

<400> SEQUENCE: 3

Met Phe Val Phe Leu Val Leu Leu Pro Leu Val

```
            65                  70                  75                  80
Asn Pro Val Leu Pro Phe Asn Asp Gly Val Tyr Phe Ala Ser Thr Glu
                    85                  90                  95
Lys Ser Asn Ile Ile Arg Gly Trp Ile Phe Gly Thr Thr Leu Asp Ser
                    100                 105                 110
Lys Thr Gln Ser Leu Leu Ile Val Asn Asn Ala Thr Asn Val Val Ile
                    115                 120                 125
Lys Val Cys Glu Phe Gln Phe Cys Asn Asp Pro Phe Leu Gly Val Tyr
                    130                 135                 140
Tyr His Lys Asn Asn Lys Ser Trp Met Glu Ser Glu Phe Arg Val Tyr
145                 150                 155                 160
Ser Ser Ala Asn Asn Cys Thr Phe Glu Tyr Val Ser Gln Pro Phe Leu
                    165                 170                 175
Met Asp Leu Glu Gly Lys Gln Gly Asn Phe Lys Asn Leu Arg Glu Phe
                    180                 185                 190
Val Phe Lys Asn Ile Asp Gly Tyr Phe Lys Ile Tyr Ser Lys His Thr
                    195                 200                 205
Pro Ile Asn Leu Val Arg Asp Leu Pro Gln Gly Phe Ser Ala Leu Glu
                    210                 215                 220
Pro Leu Val Asp Leu Pro Ile Gly Ile Asn Ile Thr Arg Phe Gln Thr
225                 230                 235                 240
Leu Leu Ala Leu His Arg Ser Tyr Leu Thr Pro Gly Asp Ser Ser Ser
                    245                 250                 255
Gly Trp Thr Ala Gly Ala Ala Ala Tyr Tyr Val Gly Tyr Leu Gln Pro
                    260                 265                 270
Arg Thr Phe Leu Leu Lys Tyr Asn Glu Asn Gly Thr Ile Thr Asp Ala
                    275                 280                 285
Val Asp Cys Ala Leu Asp Pro Leu Ser Glu Thr Lys Cys Thr Leu Lys
                    290                 295                 300
Ser Phe Thr Val Glu Lys Gly Ile Tyr Gln Thr Ser Asn Phe Arg Val
305                 310                 315                 320
Gln Pro Thr Glu Ser Ile Val Arg Phe Pro Asn Ile Thr Asn Leu Cys
                    325                 330                 335
Pro Phe Gly Glu Val Phe Asn Ala Thr Arg Phe Ala Ser Val Tyr Ala
                    340                 345                 350
Trp Asn Arg Lys Arg Ile Ser Asn Cys Val Ala Asp Tyr Ser Val Leu
                    355                 360                 365
Tyr Asn Ser Ala Ser Phe Ser Thr Phe Lys Cys Tyr Gly Val Ser Pro
                    370                 375                 380
Thr Lys Leu Asn Asp Leu Cys Phe Thr Asn Val Tyr Ala Asp Ser Phe
385                 390                 395                 400
Val Ile Arg Gly Asp Glu Val Arg Gln Ile Ala Pro Gly Gln Thr Gly
                    405                 410                 415
Lys Ile Ala Asp Tyr Asn Tyr Lys Leu Pro Asp Asp Phe Thr Gly Cys
                    420                 425                 430
Val Ile Ala Trp Asn Ser Asn Asn Leu Asp Ser Lys Val Gly Gly Asn
                    435                 440                 445
Tyr Asn Tyr Leu Tyr Arg Leu Phe Arg Lys Ser Asn Leu Lys Pro Phe
                    450                 455                 460
Glu Arg Asp Ile Ser Thr Glu Ile Tyr Gln Ala Gly Ser Thr Pro Cys
465                 470                 475                 480
Asn Gly Val Glu Gly Phe Asn Cys Tyr Phe Pro Leu Gln Ser Tyr Gly
                    485                 490                 495
```

-continued

```
Phe Gln Pro Thr Asn Gly Val Gly Tyr Gln Pro Tyr Arg Val Val Val
                500             505                 510
Leu Ser Phe Glu Leu Leu His Ala Pro Ala Thr Val Cys Gly Pro Lys
            515                 520             525
Lys Ser Thr Asn Leu Val Lys Asn Lys Cys Val Asn Phe Asn Phe Asn
        530                 535             540
Gly Leu Thr Gly Thr Gly Val Leu Thr Glu Ser Asn Lys Lys Phe Leu
545             550                 555                 560
Pro Phe Gln Gln Phe Gly Arg Asp Ile Ala Asp Thr Thr Asp Ala Val
                565             570                 575
Arg Asp Pro Gln Thr Leu Glu Ile Leu Asp Ile Thr Pro Cys Ser Phe
            580                 585             590
Gly Gly Val Ser Val Ile Thr Pro Gly Thr Asn Thr Ser Asn Gln Val
        595                 600             605
Ala Val Leu Tyr Gln Asp Val Asn Cys Thr Glu Val Pro Val Ala Ile
    610                 615             620
His Ala Asp Gln Leu Thr Pro Thr Trp Arg Val Tyr Ser Thr Gly Ser
625             630                 635                 640
Asn Val Phe Gln Thr Arg Ala Gly Cys Leu Ile Gly Ala Glu His Val
                645             650                 655
Asn Asn Ser Tyr Glu Cys Asp Ile Pro Ile Gly Ala Gly Ile Cys Ala
            660                 665             670
Ser Tyr Gln Thr Gln Thr Asn Ser Pro Arg Arg Ala Arg Ser Val Ala
        675                 680             685
Ser Gln Ser Ile Ile Ala Tyr Thr Met Ser Leu Gly Ala Glu Asn Ser
    690                 695             700
Val Ala Tyr Ser Asn Asn Ser Ile Ala Ile Pro Thr Asn Phe Thr Ile
705             710                 715                 720
Ser Val Thr Thr Glu Ile Leu Pro Val Ser Met Thr Lys Thr Ser Val
                725             730                 735
Asp Cys Thr Met Tyr Ile Cys Gly Asp Ser Thr Glu Cys Ser Asn Leu
            740                 745             750
Leu Leu Gln Tyr Gly Ser Phe Cys Thr Gln Leu Asn Arg Ala Leu Thr
        755                 760             765
Gly Ile Ala Val Glu Gln Asp Lys Asn Thr Gln Glu Val Phe Ala Gln
    770                 775             780
Val Lys Gln Ile Tyr Lys Thr Pro Pro Ile Lys Asp Phe Gly Gly Phe
785             790                 795                 800
Asn Phe Ser Gln Ile Leu Pro Asp Pro Ser Lys Pro Ser Lys Arg Ser
                805             810                 815
Phe Ile Glu Asp Leu Leu Phe Asn Lys Val Thr Leu Ala Asp Ala Gly
            820                 825             830
Phe Ile Lys Gln Tyr Gly Asp Cys Leu Gly Asp Ile Ala Ala Arg Asp
        835                 840             845
Leu Ile Cys Ala Gln Lys Phe Asn Gly Leu Thr Val Leu Pro Pro Leu
    850                 855             860
Leu Thr Asp Glu Met Ile Ala Gln Tyr Thr Ser Ala Leu Leu Ala Gly
865             870                 875                 880
Thr Ile Thr Ser Gly Trp Thr Phe Gly Ala Gly Ala Ala Leu Gln Ile
                885             890                 895
Pro Phe Ala Met Gln Met Ala Tyr Arg Phe Asn Gly Ile Gly Val Thr
            900                 905             910
```

-continued

Gln Asn Val Leu Tyr Glu Asn Gln Lys Leu Ile Ala Asn Gln Phe Asn
915                 920                 925

Ser Ala Ile Gly Lys Ile Gln Asp Ser Leu Ser Ser Thr Ala Ser Ala
930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
                995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Ser Glu Pro
    1250                1255                1260

Val Leu Lys Gly Val Lys Leu His Tyr Thr
    1265                1270

<210> SEQ ID NO 4
<211> LENGTH: 805
<212> TYPE: PRT
<213> ORGANISM: Homo sapiens

<400> SEQUENCE: 4

```
Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415
```

```
His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620

Lys Ser Ala Leu Gly Asp Arg Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
        675                 680                 685

Lys Asn Val Ser Asp Ile Ile Pro Arg Thr Glu Val Glu Lys Ala Ile
    690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
            740                 745                 750

Ile Val Val Gly Ile Val Ile Leu Ile Phe Thr Gly Ile Arg Asp Arg
        755                 760                 765

Lys Lys Lys Asn Lys Ala Arg Ser Gly Glu Asn Pro Tyr Ala Ser Ile
    770                 775                 780

Asp Ile Ser Lys Gly Glu Asn Asn Pro Gly Phe Gln Asn Thr Asp Asp
785                 790                 795                 800

Val Gln Thr Ser Phe
                805
```